(12) United States Patent
Chu

(10) Patent No.: US 9,539,078 B2
(45) Date of Patent: Jan. 10, 2017

(54) SYSTEMS, DEVICES AND METHODS FOR TREATING PELVIC FLOOR DISORDERS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 300 days.

(21) Appl. No.: 13/850,150

(22) Filed: Mar. 25, 2013

(65) Prior Publication Data

US 2013/0225919 A1 Aug. 29, 2013

Related U.S. Application Data

(62) Division of application No. 11/906,969, filed on Oct. 3, 2007, now abandoned.

(51) Int. Cl.
| | | |
|---|---|---|
| *A61F 2/00* | (2006.01) | |
| *A61B 17/06* | (2006.01) | |
| *A61B 17/00* | (2006.01) | |
| *A61B 17/29* | (2006.01) | |

(52) U.S. Cl.
CPC ....... *A61F 2/0045* (2013.01); *A61B 17/06066* (2013.01); *A61B 17/06109* (2013.01); *A61B 2017/00805* (2013.01); *A61B 2017/06042* (2013.01); *A61B 2017/06076* (2013.01); *A61B 2017/06085* (2013.01); *A61B 2017/2927* (2013.01)

(58) Field of Classification Search
CPC ......... A61F 2/0031–2/0045; A61F 2002/0072; A61B 17/06109
USPC ................................................ 600/29–31, 37
See application file for complete search history.

(56) References Cited

U.S. PATENT DOCUMENTS

| | | | |
|---|---|---|---|
| 2001/0010008 A1 | 7/2001 | Gellman et al. | |
| 2003/0078468 A1* | 4/2003 | Skiba ................. | A61B 17/0401 600/37 |
| 2003/0176762 A1* | 9/2003 | Kammerer ...................... | 600/30 |
| 2003/0220538 A1* | 11/2003 | Jacquetin ........................ | 600/37 |
| 2004/0039453 A1* | 2/2004 | Anderson et al. ......... | 623/23.72 |
| 2004/0249397 A1* | 12/2004 | Delorme et al. ............... | 606/151 |
| 2005/0250977 A1* | 11/2005 | Montpetit et al. .............. | 600/29 |
| 2006/0015069 A1 | 1/2006 | Evans et al. | |
| 2006/0089525 A1* | 4/2006 | Mamo et al. ................... | 600/37 |
| 2006/0229596 A1* | 10/2006 | Weiser et al. ................... | 606/37 |
| 2006/0260618 A1* | 11/2006 | Hodroff et al. ............... | 128/830 |

OTHER PUBLICATIONS

Office Action for EP Application No. 07839265.1, mailed Jun. 10, 2015, 6 pages.

* cited by examiner

*Primary Examiner* — Catherine B Kuhlman
(74) *Attorney, Agent, or Firm* — Brake Hughes Bellerman LLP

(57) ABSTRACT

Disclosed are implants for pelvic floor repair and related uses, and devices, kits, and methods which can be used to deliver the implants. In certain embodiments, the devices are used to deliver extensions of a surgical implant to respective target tissue regions of the levator ani muscle and the sacrospinous ligament.

21 Claims, 19 Drawing Sheets

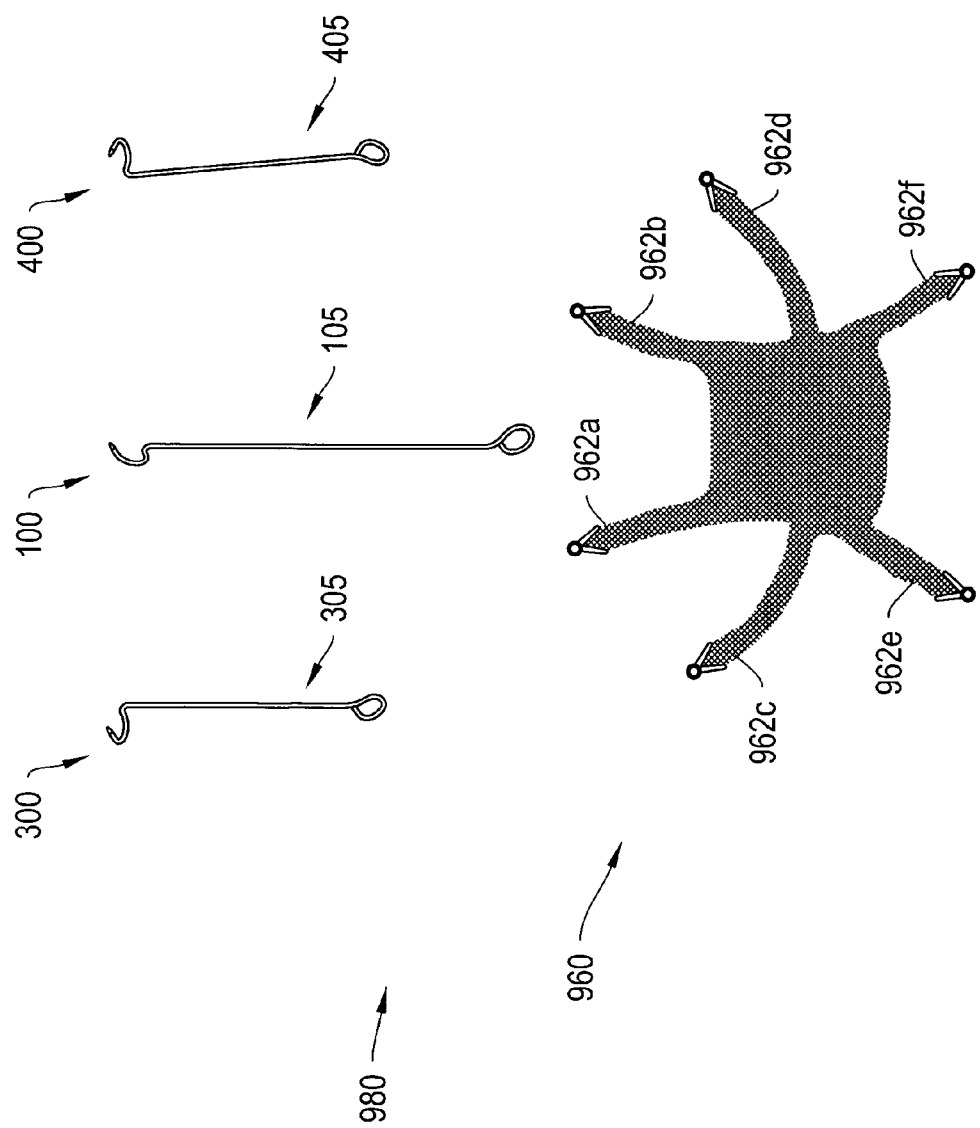

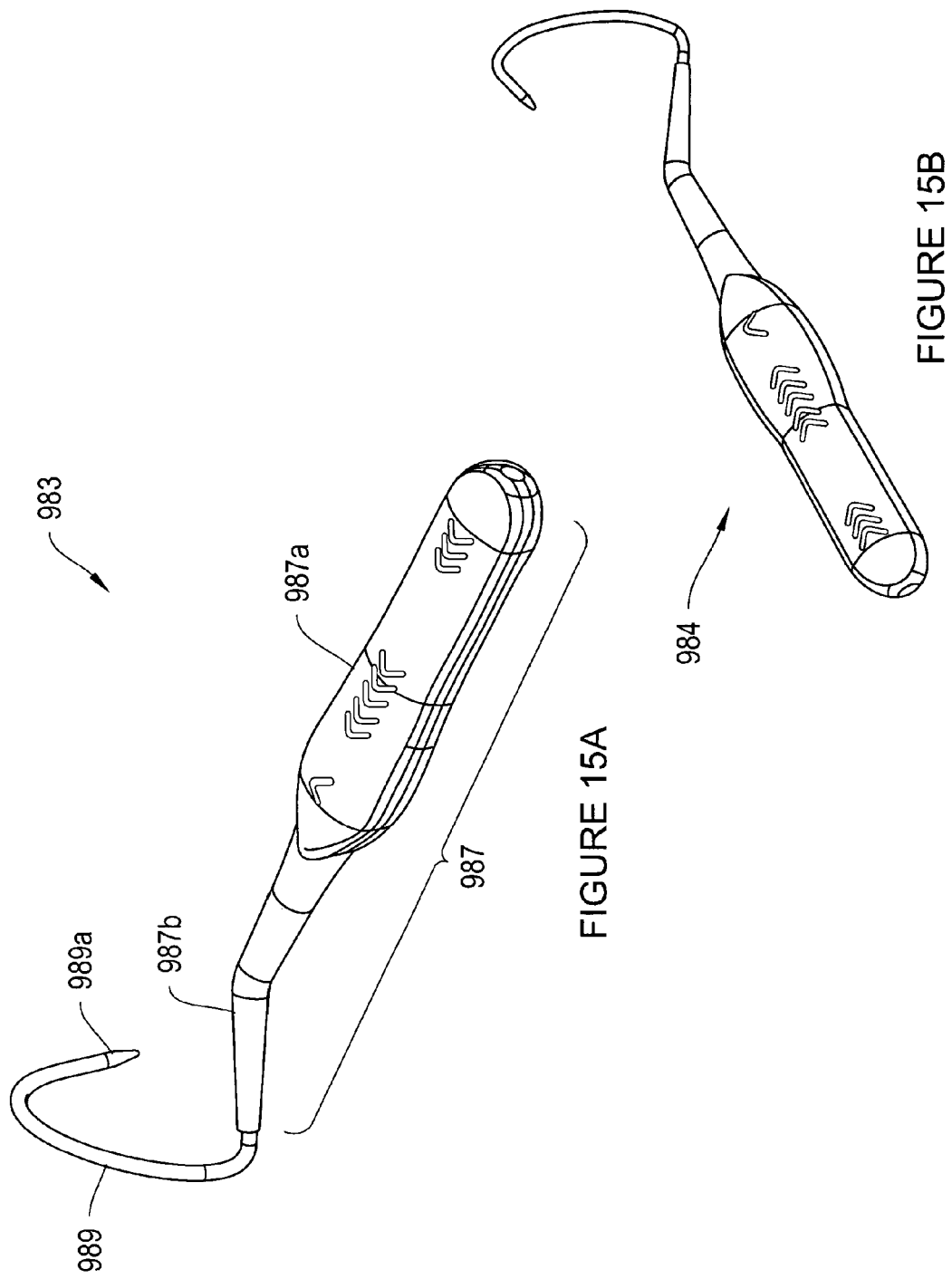

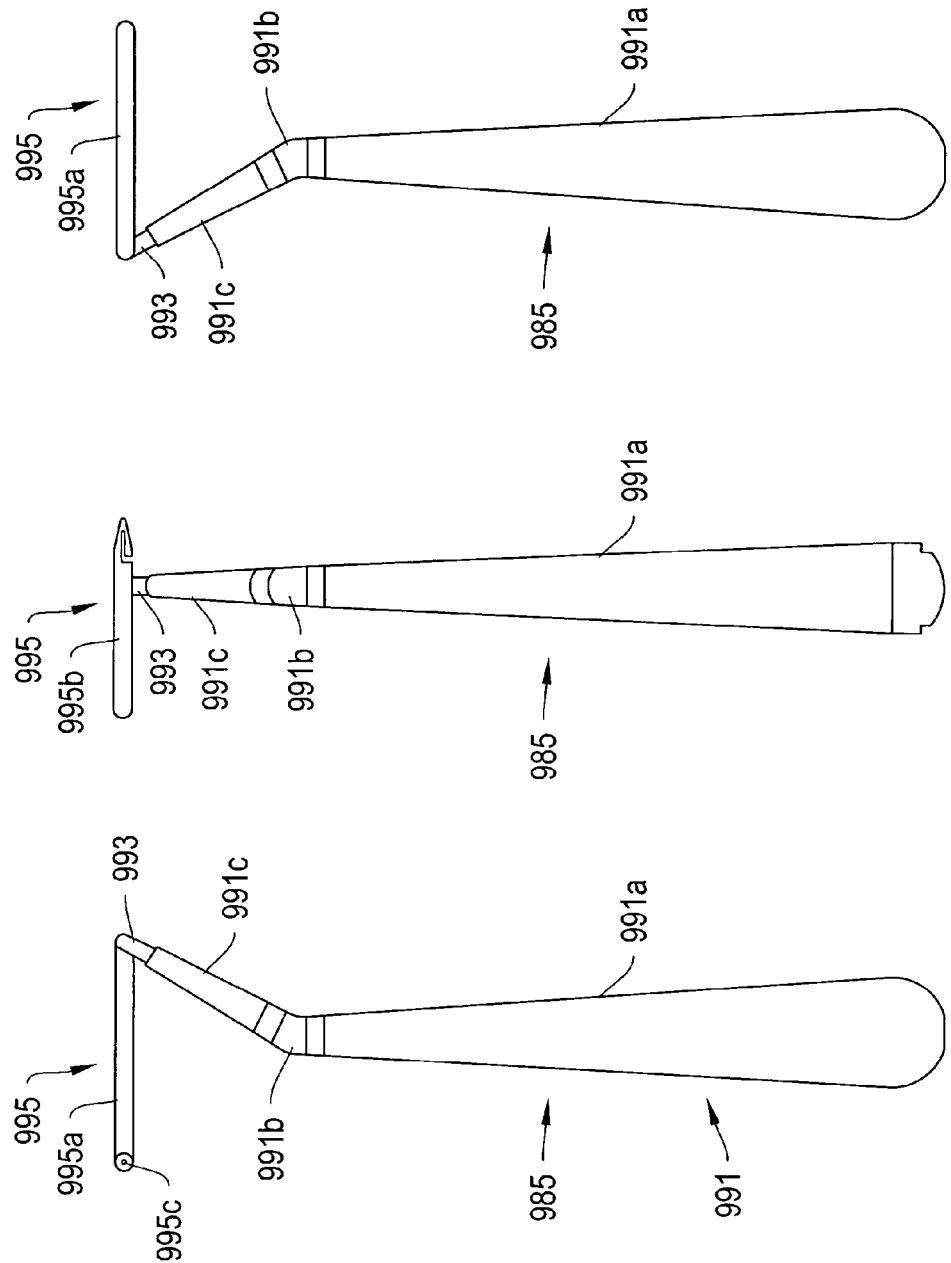

SYSTEMS, DEVICES AND METHODS FOR TREATING PELVIC FLOOR DISORDERS

RELATED APPLICATIONS

This application is a divisional of U.S. application Ser. No. 11/906,969, filed Oct. 3, 2007, the entire contents of which are incorporated by reference herein.

BACKGROUND

Pelvic floor disorders afflict many women. According to some studies, about 1 out of 11 women needs surgery for a pelvic floor disorder during her lifetime. The pelvic floor generally includes muscles, ligaments, and tissues that collectively act to support anatomical structures of the pelvic region, including the uterus, the rectum, the bladder, and the vagina. Pelvic floor disorders include vaginal prolapse, vaginal hernia, cystocele, rectocele, and enterocele. Such disorders are characterized in that the muscles, ligaments and/or tissues are damaged, stretched, or otherwise weakened, which causes the pelvic anatomical structures to fall or shift and protrude into each other or other anatomical structures.

Moreover, pelvic floor disorders often cause or exacerbate female urinary incontinence (UI). One type of UI, called stress urinary incontinence (SUI), affects primarily women and is generally caused by two conditions—intrinsic sphincter deficiency (ISD) and hypermobility. These conditions may occur independently or in combination. In ISD, the urinary sphincter valve, located within the urethra, fails to close (or "coapt") properly, causing urine to leak out of the urethra during stressful activity. In hypermobility, the pelvic floor is distended, weakened, or damaged, resulting in increases in intra-abdominal pressure (e.g., due to sneezing, coughing, straining, etc.) and consequently the bladder neck and proximal urethra rotate and descend. As a result, the urethra does not close with sufficient response time, and urine leaks through the urethra.

UI and pelvic floor disorders, which are usually accompanied by significant pain and discomfort, are typically treated by implanting a supportive sling in or near the pelvic floor region to support the fallen or shifted anatomical structures or to, more generally, strengthen the pelvic region by, for example, promoting tissue ingrowth. Often, treatments of stress incontinence are made without treating the pelvic floor disorders at all, potentially leading to an early recurrence of the pelvic floor disorder.

Existing devices, methods, and kits for treatment typically apply delivery devices to position a supportive sling into a desired position in the pelvic region. However, these devices may be difficult for a surgeon to manipulate within the posterior pelvic region without adversely affecting surrounding anatomical structures during the delivery process. Moreover, when treating pelvic floor disorders and UI it is desirable to anchor the sling to a plurality of locations in the pelvic region, but most commonly available surgical kits do not provide devices that are suitably sized and/or shaped. Thus, surgeons have limited ability to access different locations in the pelvic region. Accordingly, medical operators and patients need improved systems, methods, and surgical kits for the treatment of pelvic floor disorders and/or urinary incontinence.

SUMMARY

The invention generally pertains to devices, systems, and methods to deliver surgical implants within patients. The devices include delivery devices which can be used to implant a supportive mesh in the pelvic region of a patient for pelvic floor repair and/or for treatment of urinary incontinence. The devices also include surgical implants that are sized, shaped, and constructed to support various organs within the pelvic region of a patient, or more generally to promote tissue growth within and generally stabilize the pelvic region.

In one aspect, the invention includes a delivery device for delivering an implantable sling to an anatomical location within a patient. The devise includes a shaft having a distal end and a proximal end, a head having a curved region, a tip disposed at a distal end of the curved region, and a substantially linear region at a proximal end of the curved region, and a curved junction connecting the proximal end of the curved region and the distal end of the shaft, wherein an axis of the substantially linear region is perpendicular to a longitudinal axis of the shaft.

In another implementation, the delivery device includes a shaft having a distal end and a proximal end, a rotatable head distal to the shaft including a tip at a distal end of the head, and a pivotable junction connecting the head and the shaft. The rotatable head may include a curved region. In one feature, the rotatable head is rotatable about the distal end of the shaft. The curved regions may be semi-circular.

In one configuration, the tips employed with the device are equiplanar with the longitudinal axis of the shaft portion. In another configuration, the head lies in a plane, and the longitudinal axis of the shaft portion is normal to the plane. For example, the head may extend in a counterclockwise path from the distal end of the shaft, or the head may extend in a clockwise path from the distal end of the shaft. In other configurations, the head lies in a plane, and the longitudinal axis of the shaft has a non-normal incidence with the plane. The device may be used to implant a sling within a patient. The device may include other components such as stopping mechanisms, implant associators, and soft tissue anchors adapted to aid the implantation of the sling.

In another aspect, the invention includes methods for delivering to a patient an implant having a central region and at least four extension/appendage regions. The methods include securing a first extension of the implant to at least one of a sacrospinous ligament, a coccygeus muscle, an ischiococcygeus muscle, an iliococcygeus muscle, and a levator ani muscle on a first side of a patient, securing a second extension of the implant to at least one of a sacrospinous ligament, a coccygeus muscle, an ischiococcygeus muscle, an iliococcygeus muscle, and a levator ani muscle on a contra-lateral side of the patient, delivering a third extension of the implant through an obturator foramen on the first side of the patient, and delivering a fourth extension of the implant through an obturator foramen on the contra-lateral side of the patient.

In one implementation, the methods include securing the first extension with a first delivery device, securing the second extension with a second delivery device different from the first delivery device, and delivering the third extension with a third delivery device different from the first delivery device and different from the second delivery device.

The methods may also include securing a fifth extension to at least one of a sacrospinous ligament, a coccygeus muscle, an ischiococcygeus muscle, an iliococcygeus muscle, and a levator ani muscle on the first side of a patient, and securing a sixth extension to at least one of a sacrospinous ligament, a coccygeus muscle, an ischiococcygeus muscle, an iliococcygeus muscle, and a levator ani muscle on the contra-lateral side of the patient. In one implementation, the methods contemplate the use of a plurality of devices having different lengths. In one configuration, the methods include securing a fifth extension with a delivery device different from the first delivery device, different from the second delivery device, and different from the third delivery device.

In one feature, the methods include associating the respective first or second extension with a delivery device including a head, the head portion including a tip, and driving the tip of the delivery device through the respective sacrospinous ligament, coccygeus muscle, or levator ani muscle. This may include placing the tip against the respective sacrospinous ligament, coccygeus muscle, or levator ani muscle, and applying pressure directly on the head. In one feature, at least one of securing the first extension and securing the second extension may include suturing the respective first or second extension to the respective sacrospinous ligament, coccygeus muscle, or levator ani muscle.

In an additional aspect, the invention includes a surgical kit having one or more of the devices described herein for use in delivering an implant within a patient. In certain embodiments the kit includes a first delivery device having a first shaft for delivering a first implant region, and a second delivery device having a second shaft for delivering a second implant region. The kit may include a third delivery device having a third shaft for delivering a third implant region. In certain embodiments, the shafts are provided with differing lengths.

In one configuration, one shaft is more than about 20% longer than one or more other shafts in the kit. The kit may also include an implant, and optionally, other devices for assisting in the exemplary surgical procedures. Methods for associating the delivery devices with the implants, methods for delivering the implants to desired locations within a patient, and methods for positioning, tensioning, and/or fixating the implants within a patient are also contemplated. Exemplary applications of the devices and methods include the treatment of conditions such as prolapse, vaginal hernia, cystocele, rectocele, enterocele, and urinary incontinence. These and other aspects will be described herein.

BRIEF DESCRIPTION OF THE DRAWINGS

These and other features and advantages of the invention will be more fully understood by the following illustrative description with reference to the appended drawings, in which like elements are labeled with like reference designations and which may not be to scale.

FIG. 14 illustrates a surgical kit for use in pelvic floor repair.

FIGS. 15A-15B show delivery devices for delivering an anterior implant strap.

FIGS. 16A-16C show various views of a delivery device for delivering anterior implant straps.

DETAILED DESCRIPTION OF EXEMPLARY EMBODIMENTS

The devices, methods, and kits of this invention are generally used to deliver a surgical implant, such as an implantable sling, to the pelvic region of a patient for pelvic floor repair and/or for treatment of urinary incontinence. The devices include improved delivery tools that are sized and shaped to deliver the surgical implant to the pelvic region, and improved surgical implants sized, shaped, and constructed to support various organs within the pelvic region, or more generally to promote tissue growth in and the general stability of the pelvic region. In certain embodiments, the implant includes a central region and a plurality of extensions, such as mesh straps, that extend from the central region and are anchored at respective locations in the pelvic region of a patient to appropriately position and/or tension the implant. The extensions are anchored to the patient's pelvic floor using delivery devices that drive the extensions through the tissues, ligaments, and/or muscle regions thereof.

The devices may be configured to allow the operator to deliver and secure the implant to posterior regions of the pelvic floor, such as the sacrospinous ligament, the coccygeus muscle, the ischiococcygeus muscle, the iliococcygeus muscle, and the tendinous arch of the levator ani muscle. Such anatomical locations are useful locations for anchoring the straps of pelvic floor implants within the pelvic region. An operator accesses these anatomical locations by guiding the devices through a vaginal incision.

Methods for associating the delivery devices with the implants, methods for delivering the implants to desired locations within a patient, and methods for positioning, tensioning, and/or fixating the implants within a patient are described.

The delivery devices used to implant the various extension need not be the same, and in one implementation, a surgical kit including three delivery devices is provided. In such implementations, each of these devices are sized and shaped to facilitate delivery to certain ones of the tissue regions.

Figure 1A:
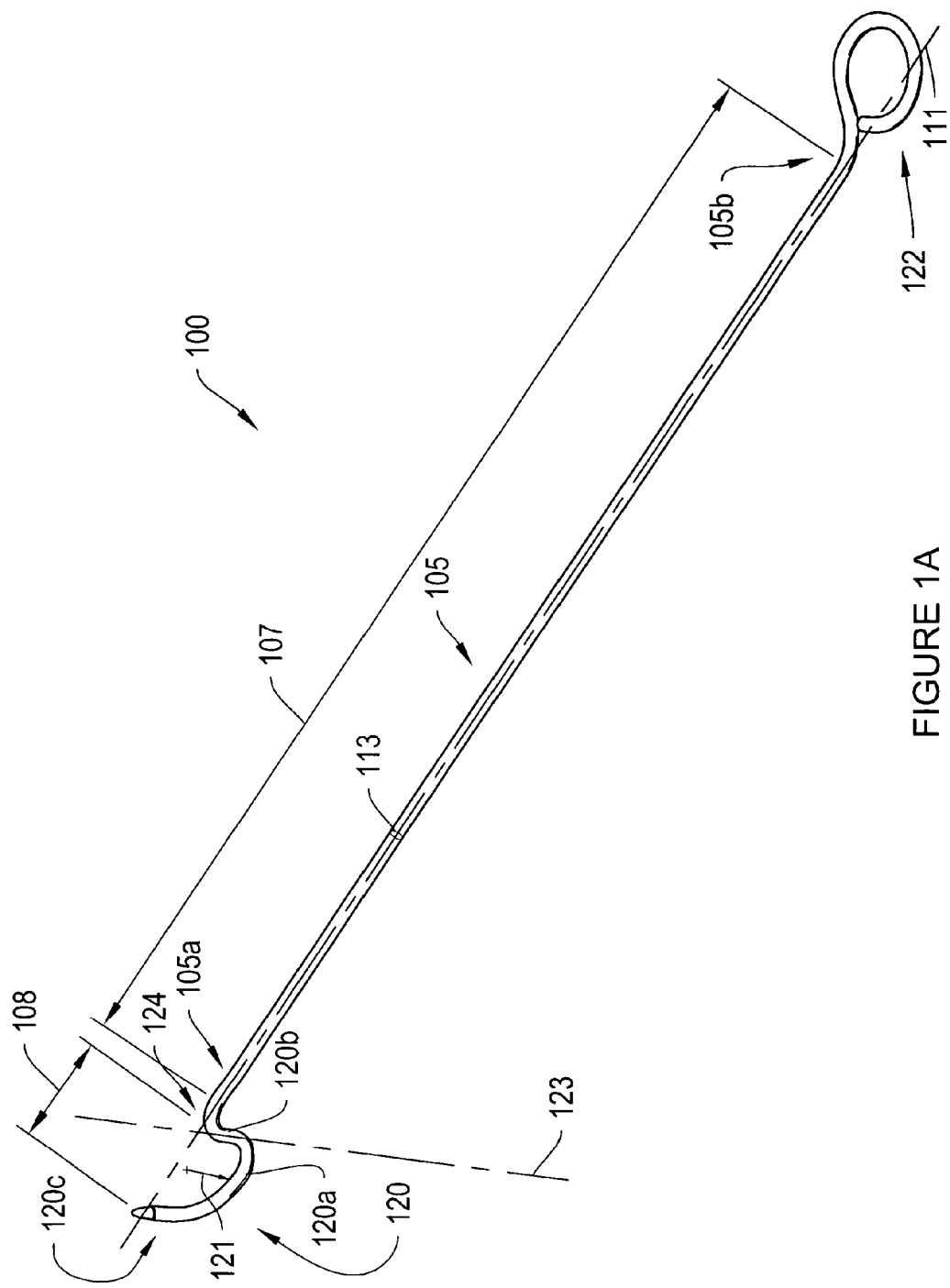
FIG. 1A shows a delivery device for delivering a pelvic floor implant to an anatomical location.

FIG. 1A depicts an exemplary embodiment of a device 100 that is adapted to deliver, through a vaginal incision, a mesh strap to a target tissue region of the sacrospinous ligament. The sacrospinous ligament is a thin and triangular tissue that is attached by its apex to the spine of the patient's ischium, and medially, by its broad base, to the lateral margins of the sacrum and coccyx in front of the sacrotuberous ligament. The sacrospinous ligament is a convenient location to anchor mesh straps in the posterior regions of the pelvic floor in order to provide posterior support.

The device 100 may also be adapted to deliver, through a vaginal incision, a mesh strap to a target tissue region of the coccygeus (or ischiococcygeus) muscle. The coccygeus muscle is a triangular muscle that originates from the ischial spine and the sacrospinous ligament and the coccyx, and inserts on the lateral aspects of the lower sacrum and the upper coccyx.

The delivery device 100 includes a shaft 105, a handle 122, a head 120 for attaching to an implant and delivering the implant to the patient's anatomy, and a curved junction 124 configured within an arc that allows the head 120 to penetrate the patient's anatomy. The shaft 105 includes a distal end 105a, a proximal end 105b, and a longitudinal axis 111. The shaft 105 has a length 107 that is substantially longer than the length 108 of the head 120. The relatively long shaft length 107 allows an operator to insert the device through the vaginal cavity of a patient and place the head 120 within the posterior pelvic region in proximity to the sacrospinous ligament or the coccygeus muscle.

Figure 1B:
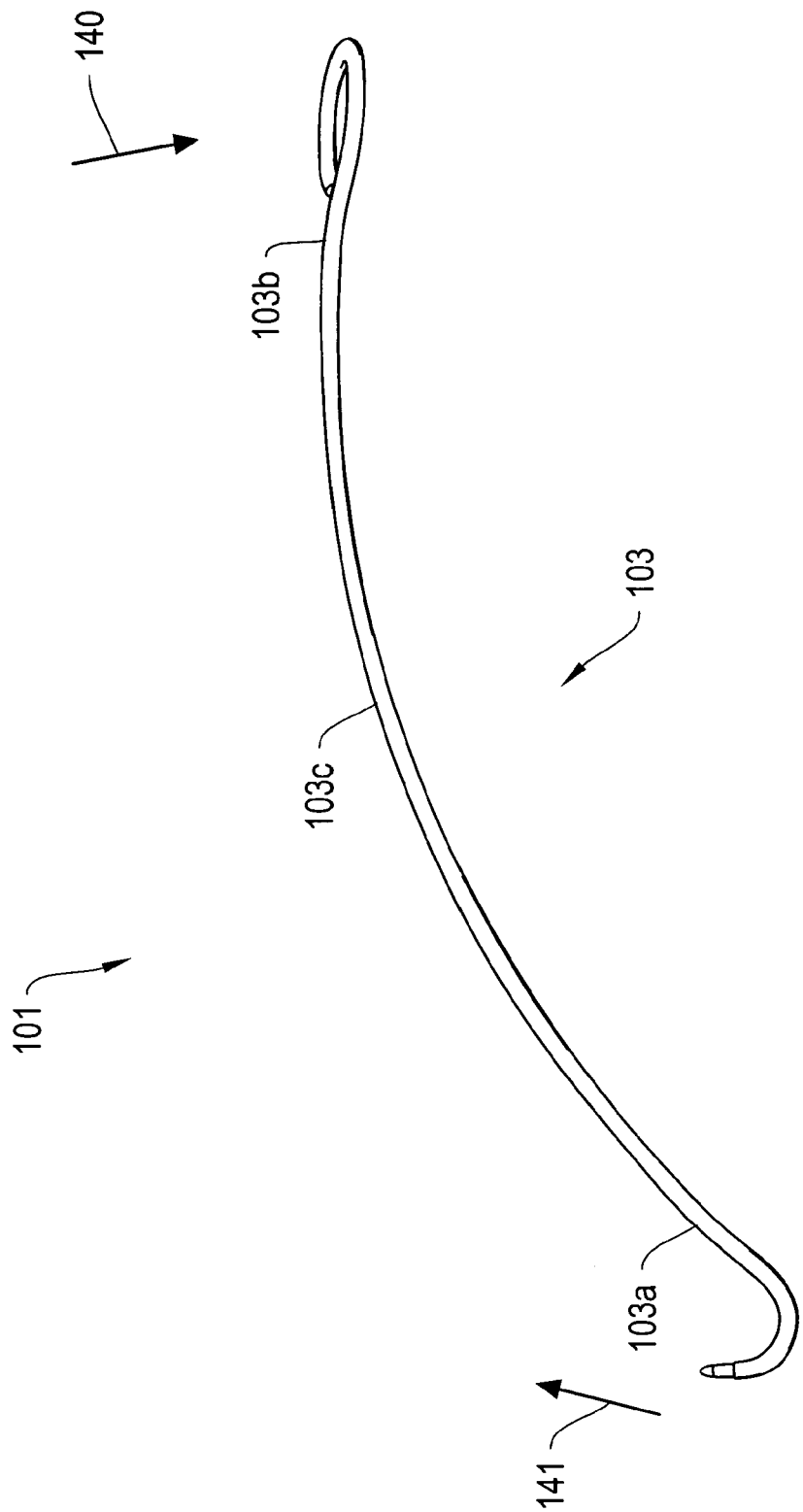
FIG. 1B illustrates another embodiment of a delivery device for delivering a pelvic floor implant to an anatomical location.

The shaft 105 is shown to be substantially linear, but it may be slightly curved to form either a convex or a concave arc to further facilitate delivery of the head. FIG. 1B illustrates an alternate embodiment 101 of the delivery device 100 of FIG. 1A having a curved shaft 103 instead of the linear shaft 105 of FIG. 1A. The curved shaft 103 may facilitate passage of the device through the vaginal canal to access the sacrospinous ligament or coccygeus muscle of the patient. In addition, the curved shaft allows rotation of the delivery device 101 for insertion of the head 120 into the patient's tissues. This may be done, for example, by applying a force in direction 140 to the proximal end 103b of the device 101 thereby rotating the device about the middle area 103c of the shaft 103 such that the distal end 103a of the shaft 103 and the head 120 rotate into the tissues in the direction 141. The amount of curvature will typically be chosen to facilitate delivery of the device into the patient using a preferred method and path of insertion, described in exemplary embodiments below.

Referring again to FIG. 1A, the shaft 105 also has a circular cross-section 113 with a radius selected as needed to suit an intended path and location for delivery of the implant. In certain embodiments, the radius is about 0.05 inches, about 0.0625 inches, or about 0.075 inches which allows the device 100 to be inserted through a vaginal incision and into the sacrospinous ligament or coccygeus muscle, as described more particularly in connection with FIGS. 13A-13B. In certain embodiments, the radius is about 0.5 inches or less. In certain embodiments, the radius is about 0.125 inches. In certain embodiments, the radius is between about 0.01 inches and about 0.5 inches, or as otherwise desired to aid in implantation within other pelvic floor areas.

As noted, the device includes a handle 122 that is configured to allow an operator to grasp and manipulate the device as required to deliver a surgical implant to a desired location in a patient's anatomy.

The handle 122 is generally a looped region of the shaft 105 at the proximal end 105b of the shaft 105. However, the depicted handle 122 is not intended to be limiting and other suitable handle configurations can be used. By way of example, the device 100 can include the handle 119 of the device 300 illustrated in FIG. 8. The handle 119 is sized and shaped to be comfortably grasped and manipulated by an operator. The handle can be made of a single material, or a combination of materials. Exemplary materials include acrylonitrile butadiene styrene and soft durometer TPE. Other suitable materials may be used, including thermoplastic materials and other materials suitable for surgical environments.

As noted, the device 100 includes a head 120 that is configured to enable an operator to deliver and secure an implant to a desired anatomical structure in the body, such as a region of the sacrospinous ligament, coccygeus muscle, or other positions within the pelvic region. More particularly, the head 120 includes a curved region 120a, a substantially linear region 120b at a proximal end of the curved region 120a, and an end region 120c at a distal end of the curved region 120a. The depicted curved region 120a is C-shaped. It can alternatively be semi-elliptical, and in certain embodiments semi-circular with a radius of curvature 121 of between about 0.125 inches and about 0.75 inches, though this length can be larger or smaller as desired. The substantially linear region 120b of the head 120 is configured to have a desired length. The region 120b shown in FIG. 1A is between about 0.125 inches and about 0.5 inches in length to allow the head 120 to fit properly through the sacrospinous ligament or coccygeus muscle, though this length can be larger or smaller as desired. The substantially linear region 120b includes a longitudinal axis 123 oriented to be substantially perpendicular to the longitudinal axis 111 of the shaft 105. However, in alternative embodiments the axes 111 and 123 are not perpendicular, but intersect at angles of about 90° or at an angle chosen to suit an intended path and location for delivery of the implant. In certain embodiments, the length 107 of the shaft 105 along the axis 111 is about ten times longer than the length 108 of the head 120 along the axis 111.

Figure 2A:
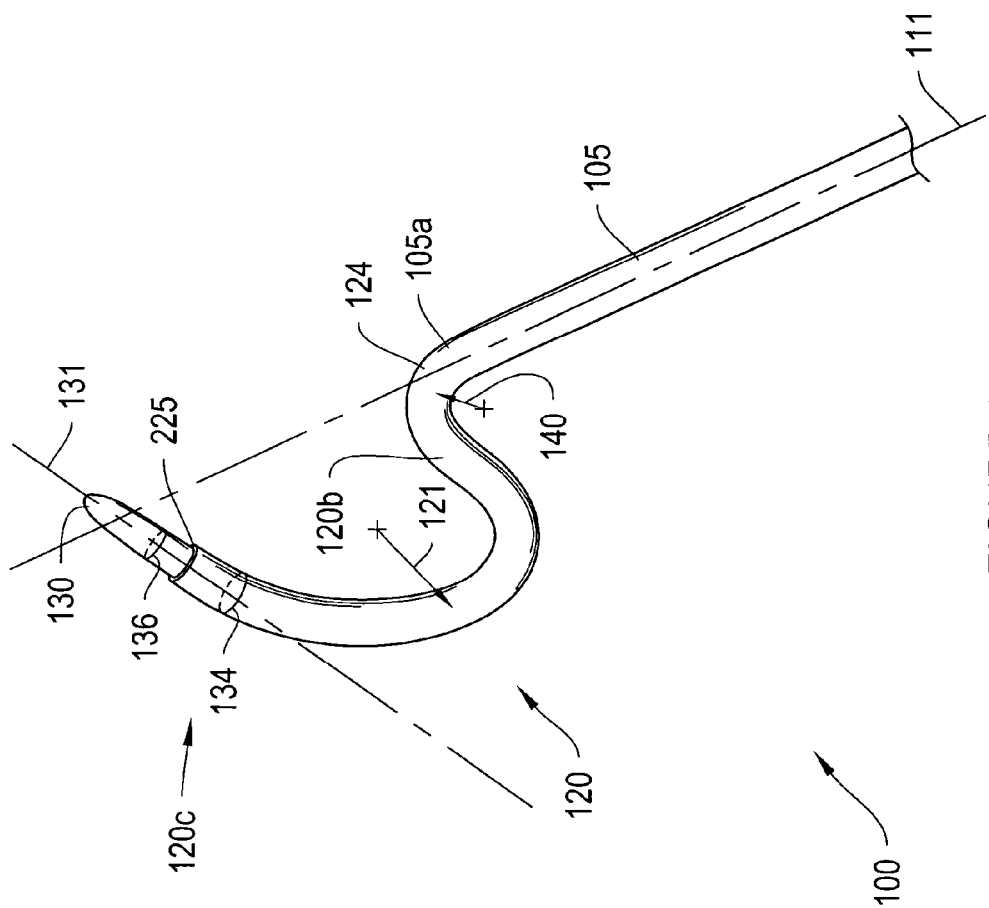
FIGS. 2A-2B show close-up views of the head portions of an exemplary pelvic floor delivery device.
Figure 2B:
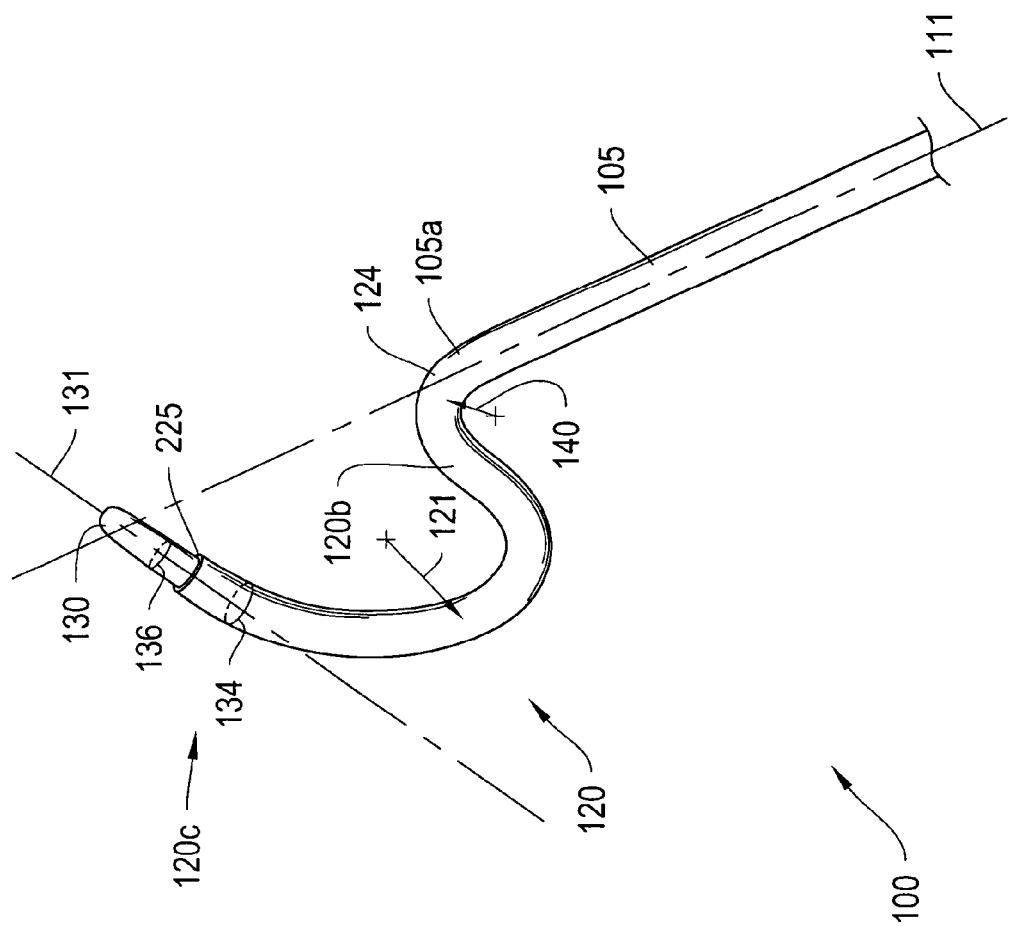

As noted, the head 120 also includes an end region 120c. FIG. 2A shows a close-up view of the head 120 of the device 100 and in particular, the end region 120c. As shown, the end region 120c has a tip 130 that extends along a longitudinal axis 131 which intersects the longitudinal axis 111 of the shaft 105, such that the end of the tip 130 is substantially equiplanar with the longitudinal axis 111. The tip 130 is sharp and configured to dissect tissue material, including contractile tissue, epithelium, and/or connective tissue. The tip 130 is preferably sharp enough to dissect muscle and ligament. As discussed below, in one exemplary method, the tip 130 is associated with an implant and driven through a target region in the sacrospinous ligament, coccygues muscle, iliococcygeus muscle, and/or the levator ani muscle. In alternate embodiments, as depicted in FIG. 2B, the tip 130 is blunt, allowing for the blunt dissection of tissue.

As shown in FIG. 2A, the tip 130 further includes a shoulder 225 which provides a stopping mechanism for an implant associator of a surgical implant, as discussed below with reference to FIGS. 5-6. As illustrated, the shoulder 225 is generally shaped as a circular step that juts out from the tip 130, resulting in the end-region 120c having varying cross-sections. More specifically, a cross section 134 of the device taken in a location proximal to the shoulder (i.e., away from the tip) has a larger radius than a radius of a cross section 136 of the device taken in a location just distal to the shoulder (i.e., toward the tip).

With continued reference to FIG. 2A, the device 100 also includes a junction 124 that connects the head 120 and the shaft 105, and in particular connects the substantially linear region 120b of the head 120 to the distal end 105a of the shaft 105. The depicted junction 124 is curved. In certain embodiments, the junction 124 has a radius of curvature 140 between about 0.1 inches and about 0.7 inches. The radius of curvature 140 may be smaller or larger than the radius of curvature 121 of the curved region 120a. The junction 124 alternatively need not be curved at all. Instead, the junction 124 may include an angled junction formed by the substantially linear region 120b and the shaft 105, with no intervening curvature. The appropriate radius of curvature 140 or angle of the junction 124 can be chosen to suit a preferred method and location of delivery of the surgical implant. As discussed below, the junction 124 may also include a hinge about which the head 120 is rotatable.

Figure 3:
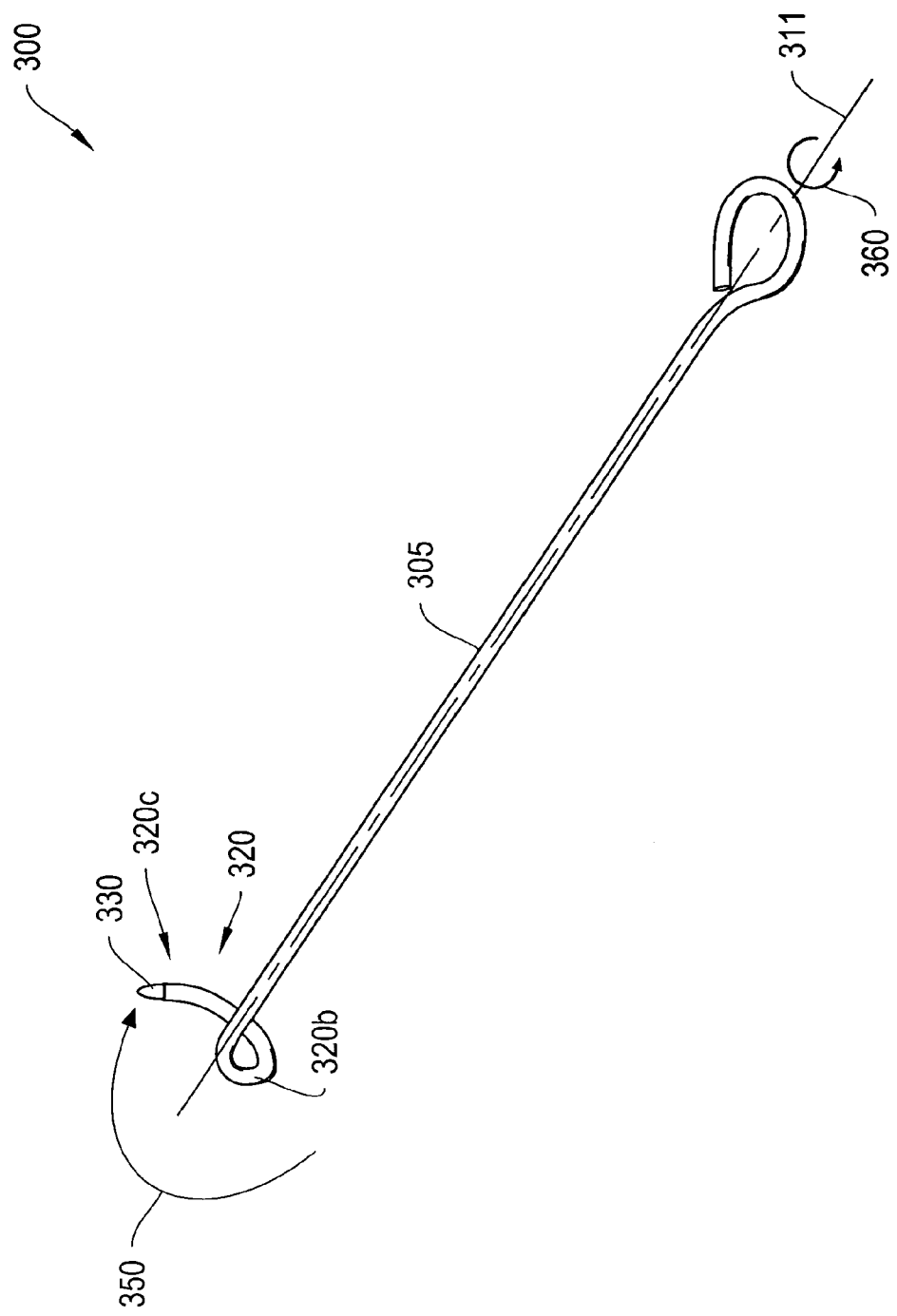
FIG. 3 shows an alternative embodiment of an exemplary pelvic floor delivery device having a head oriented perpendicularly to a shaft.

FIG. 3 shows an alternative embodiment 300 of the device of FIG. 1A having a head 320 oriented perpendicularly to the shaft 305 to allow the operator to deliver a surgical implant to a region of a patient's levator ani muscle, such as the tendinous arch of the levator ani or the iliococcygeus muscle, through a vaginal incision. The levator ani muscle is a broad, thin muscle situated generally on the side of the pelvis that is attached to the inner surface of the lesser pelvis. It is a convenient location to anchor mesh straps in order to provide lateral and/or posterior support and tension for a surgical implant. The iliococcygeus is a portion of the levator ani muscle originating from the ischial spine and the arcus tendineus levator ani and sloping inferiorly toward the midline. The iliococcygeus includes fibers that blend with the longitudinal muscle of the rectum.

As shown, the delivery device 300 is similar to the device 100, but its head 320 is positioned about 90 degrees clockwise 350 with respect to the operator of the device to allow the head 320 to align next to the levator ani muscle when the device 300 is passed through a vaginal incision. Generally, the head 320 of the device 300 lies substantially in a plane, and the longitudinal axis 311 of the shaft 305 is normal to the plane. The head 320 traces a counter clockwise 360 path from its linear region 320b to its tip 330 with respect to a distally-looking vantage of the delivery device (i.e., with respect to an operator's vantage). This configuration allows the operator to position the implant through a vaginal incision next to the levator ani muscle so the head 120 (coupled to the implant strap) can be driven into the muscle, thereby inserting the strap into the muscle to secure the implant.

Figure 4:
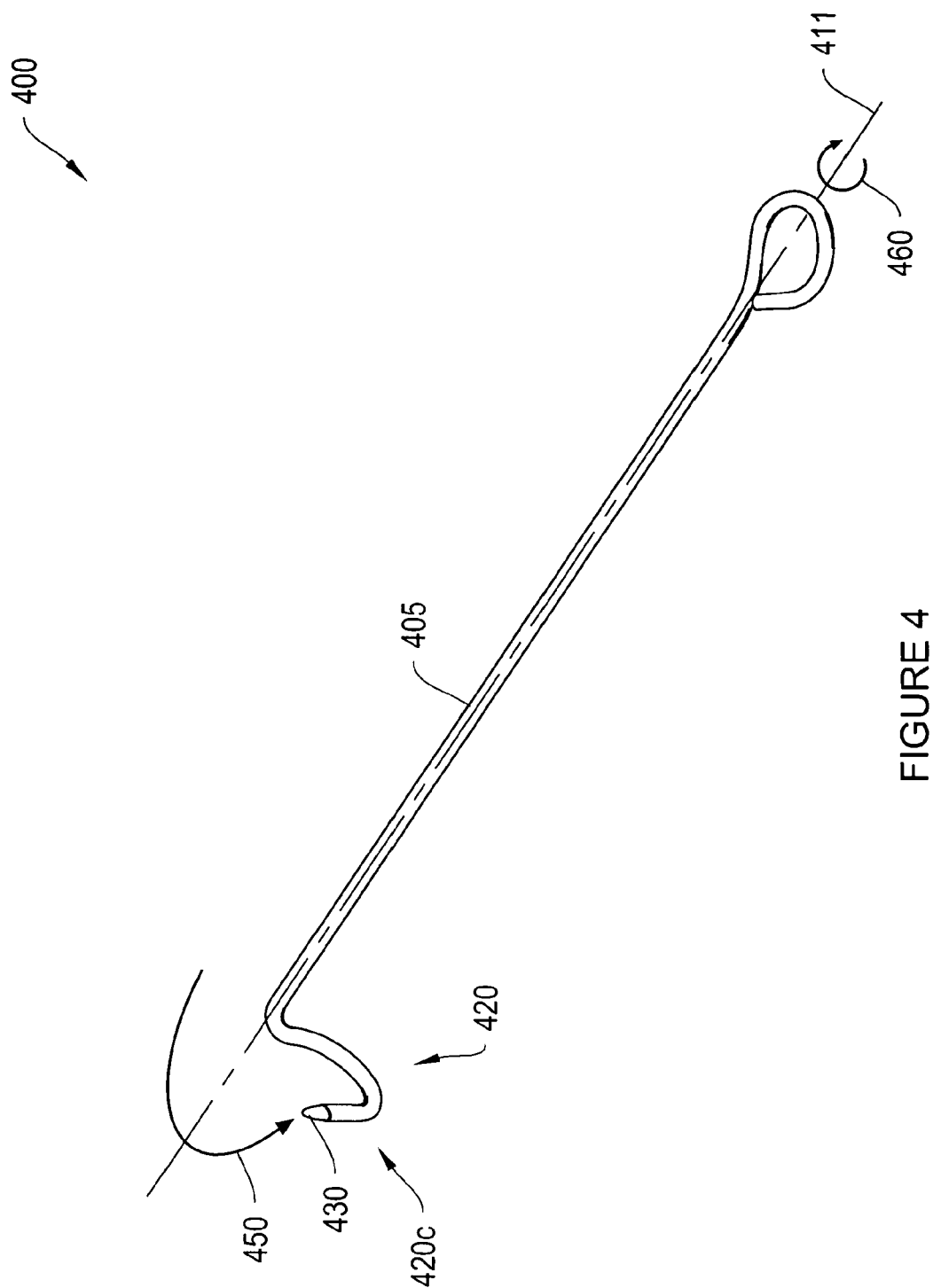
FIG. 4 shows an alternative configuration of the device of FIG. 3 having a head oriented on a contra-lateral side of the shaft.

FIG. 4 shows an alternative embodiment 400 of the device 100 of FIG. 1a having a head 420 oriented on the contra lateral side of its shaft 405 compared to the head 320 and shaft 305 of FIG. 3. The device 400 is then suited to deliver a surgical implant, such as a pelvic floor mesh strap, to a region of a patient's levator ani muscle contra-lateral to the region of the levator ani muscle discussed with respect to FIG. 3. More particularly, the delivery device 400 is similar to the device 100, but with the head 420 rotated by about 90 degrees counterclockwise 450 with respect to the operator of the device. Generally, the head 420 of the device 400 lies substantially in a plane, and the longitudinal axis 411 of the shaft 405 is normal to the plane. The head 420 traces a clockwise 460 path from the linear region 420b to the tip 430, with respect to a distally-looking vantage of the delivery device (i.e., with respect to an operator's vantage). This configuration allows the operator to position the implant through a vaginal incision and next to the levator ani muscle, so the head 120 (with the implant strap) can be driven into the muscle, thereby inserting the strap into the muscle to secure the implant.

In other embodiments not illustrated, the head can be rotated by more or less than 90 degrees in either the counterclockwise 450 or clockwise 350 directions to allow the implant or its straps to be inserted within any ligaments, muscles or other desired pelvic tissues. In these cases, the heads will lie substantially in a plane, and the respective longitudinal axes of the shaft will have a non-normal incidence with the plane. The appropriate incidence angle can be chosen to facilitate insertion of the device using a preferred method and location for delivery.

In certain embodiments, the shafts 305 and 405 of the delivery devices 300 and 400, respectively, are of about equal length and are shorter in length than the shaft 105 of the delivery device 100. This is beneficial because the sacrospinous ligament and coccygeus muscle are located posterior to the tendinous arch of the levator ani muscle and the iliococcygeus muscle. The shafts 305 and 405 are, in certain embodiments, about 8 times longer than respective heads 320 and 420. The shaft 105 is generally between about 15% and about 50% longer than the shafts 305 and 405, and in some embodiments is about 20% longer than the shafts 305 and 405.

Figure 5:
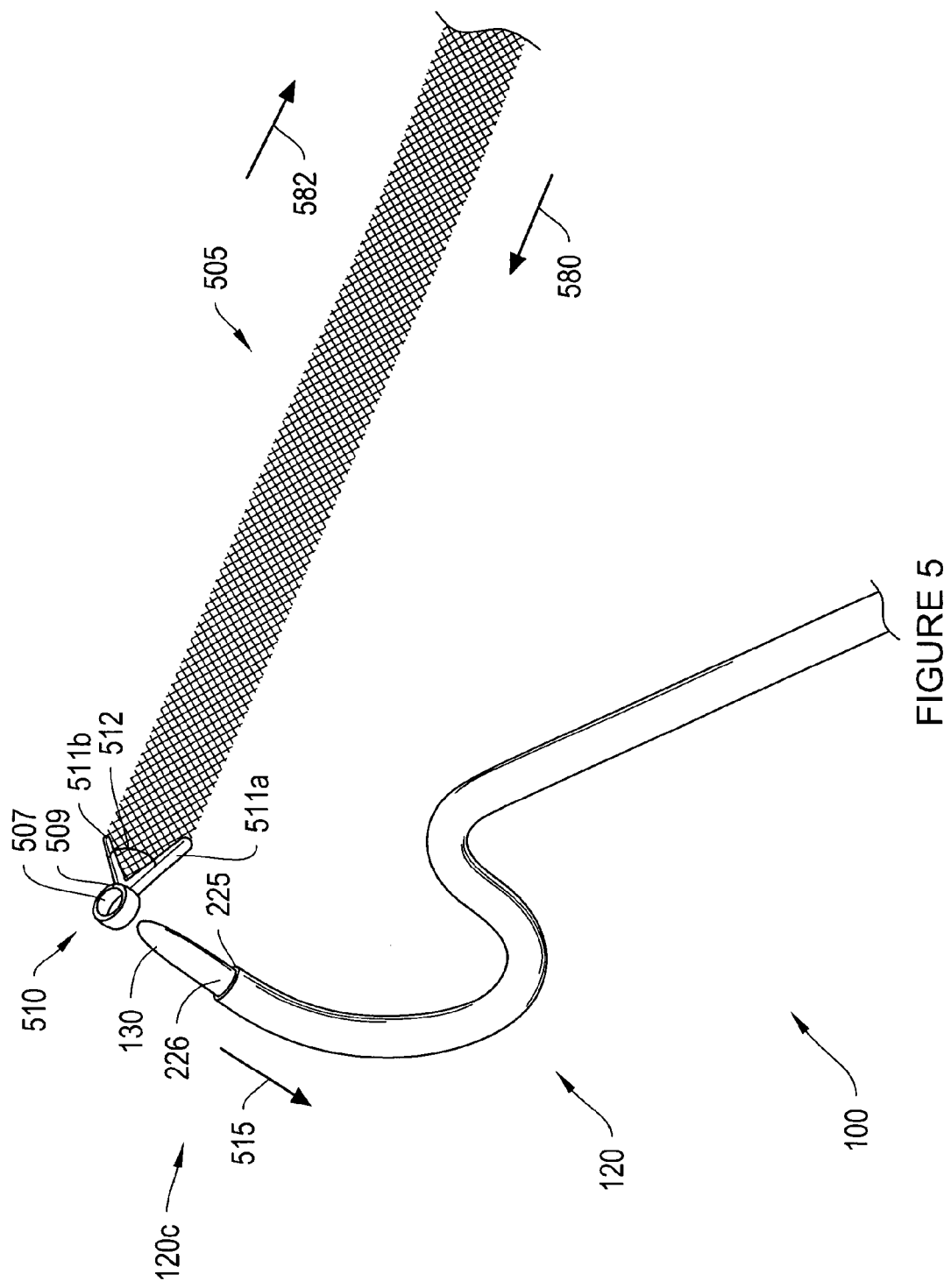
FIG. 5 shows an exemplary pelvic floor device and an implantable mesh strap assembly including an implant associator.

FIG. 5 more particularly shows an exemplary device, such as the device 100 of FIG. 1A, in operation with an implantable mesh strap assembly including an implant 505. The depicted implant 505 is a mesh strap 505 portion of a surgical implant assembly that can be used to treat pelvic floor disorders, UI, or other conditions. The implant 505 is configured to couple with the tip 130 of device 100 for delivery of the implant 505 to a target tissue region. It is to be understood that the other tips 330 and 430 of devices 300 and 400 respectively, as well as other device tips discussed herein, can be used in similar operative combinations with surgical implants such as mesh strap 505.

As shown, the mesh strap 505 includes an implant associator 510 for associating with the tip 130 of the delivery device 100, and in certain embodiments the implant associator 510 also anchors the mesh strap 505 in tissue. The depicted implant associator 510 has a ring 509 and wings 511a and 511b. In operation, an operator places the ring 509 over the tip 130 and the ring 509 slides down the tip 130 until the ring 509 abuts the shoulder 225. The step or shoulder 225 of the end-region 120c prevents passage of the ring 509 in a direction that is proximal and further down 515 along the delivery device.

The ring 509 includes an inner surface 507 that is tapered, and thereby the ring 509 inter-fits with the outer surface 226 of the tip 130. The depicted ring 509 is coplanar with the mesh strap 505.

The wings 511a and 511b of the implant associator 510 extend radially from the ring 509 and form an angle 512. The angle allows the wings 511a and 511b to be inserted within a patient's tissue to secure the mesh strap 505 in a desired location. In one embodiment, the implant associator 510 is flexible such that the angle 512 can be increased or decreased upon application of appropriate mechanical pressure. By way of example, if the mesh strap 505 is passed through tissue in a forward direction 580, the wings 511a and 511b interact with the tissue to reduce the angle 512. If the mesh strap 505 is passed through tissue in a retrograde direction 582, the wings 511a and 511b interact with the tissue to increase the angle 512. The varying angle 512 facilitates movement of the mesh strap 505 in the forward direction 580, and impedes movement of the mesh strap 505 in the retrograde direction 582. The angle 512 formed between the wings 511a and 511b can be configured so that it varies, as can the flexibility of the connector 505. These properties are generally chosen to suit the particular delivery path location for delivering the implant, as well as the condition being treated. In certain exemplary embodiments, wings 511a-b are not included and the ring 509 is molded, glued or otherwise affixed to the mesh so that, by itself, it couples the mesh strap 505 and the end region 120c. The ring 509 of implant associator 510 can have varying thicknesses and/or varying lengths.

Figure 6:
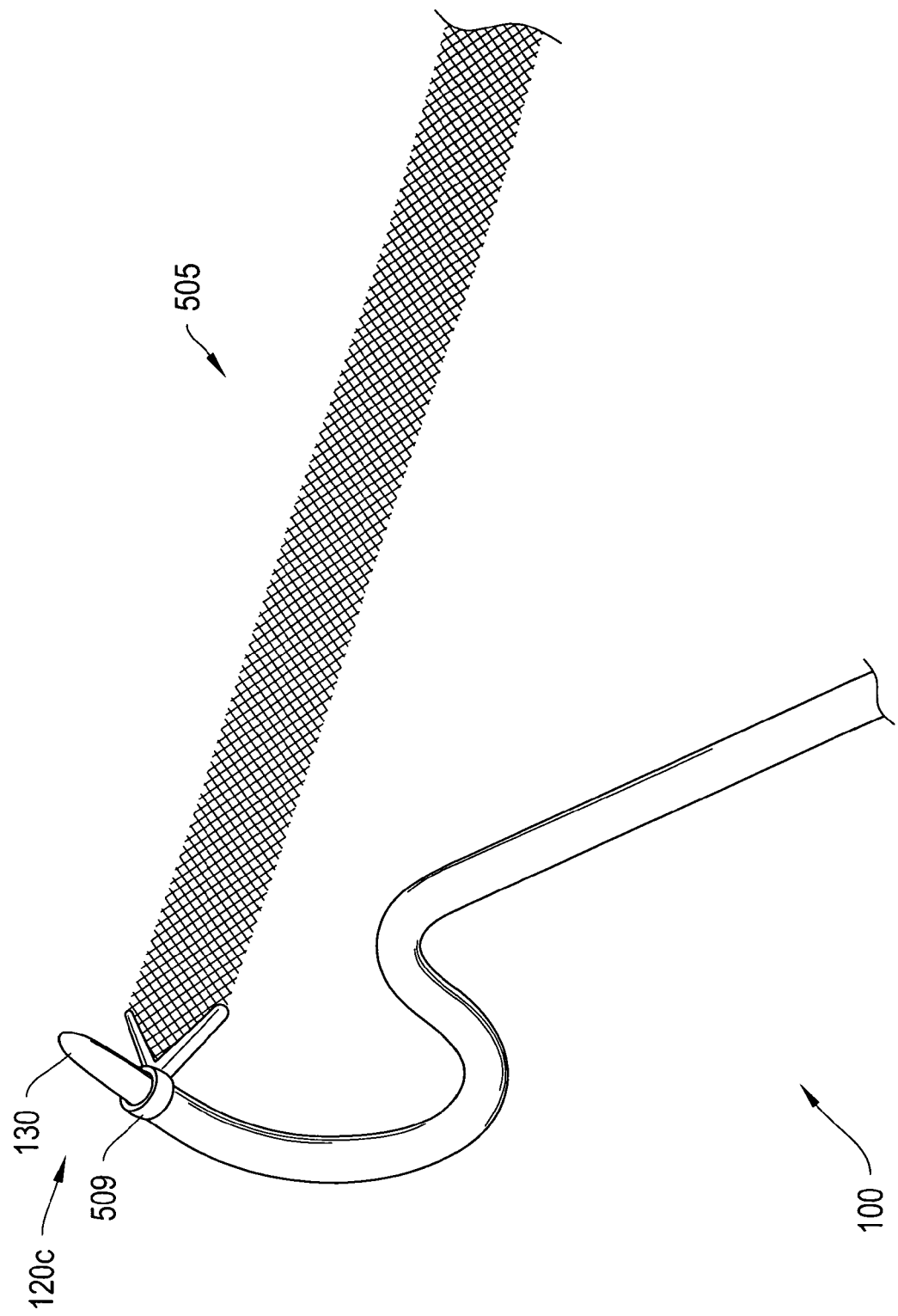
FIG. 6 shows the delivery device of FIG. 5 coupled with the mesh strap of FIG. 5.

FIG. 6 shows the delivery device 100 coupled with the mesh strap 505 of FIG. 5. The end-region 120c of the device 100 protrudes through the ring 509 even after the device 100 has been associated with the mesh strap 505. This allows the delivery device 100 to dissect tissue as it implants the mesh strap 505. In operation, the tip 130 of the device is pushed into the tissue and the associated ring 509 follows into the tissue.

Figure 7:
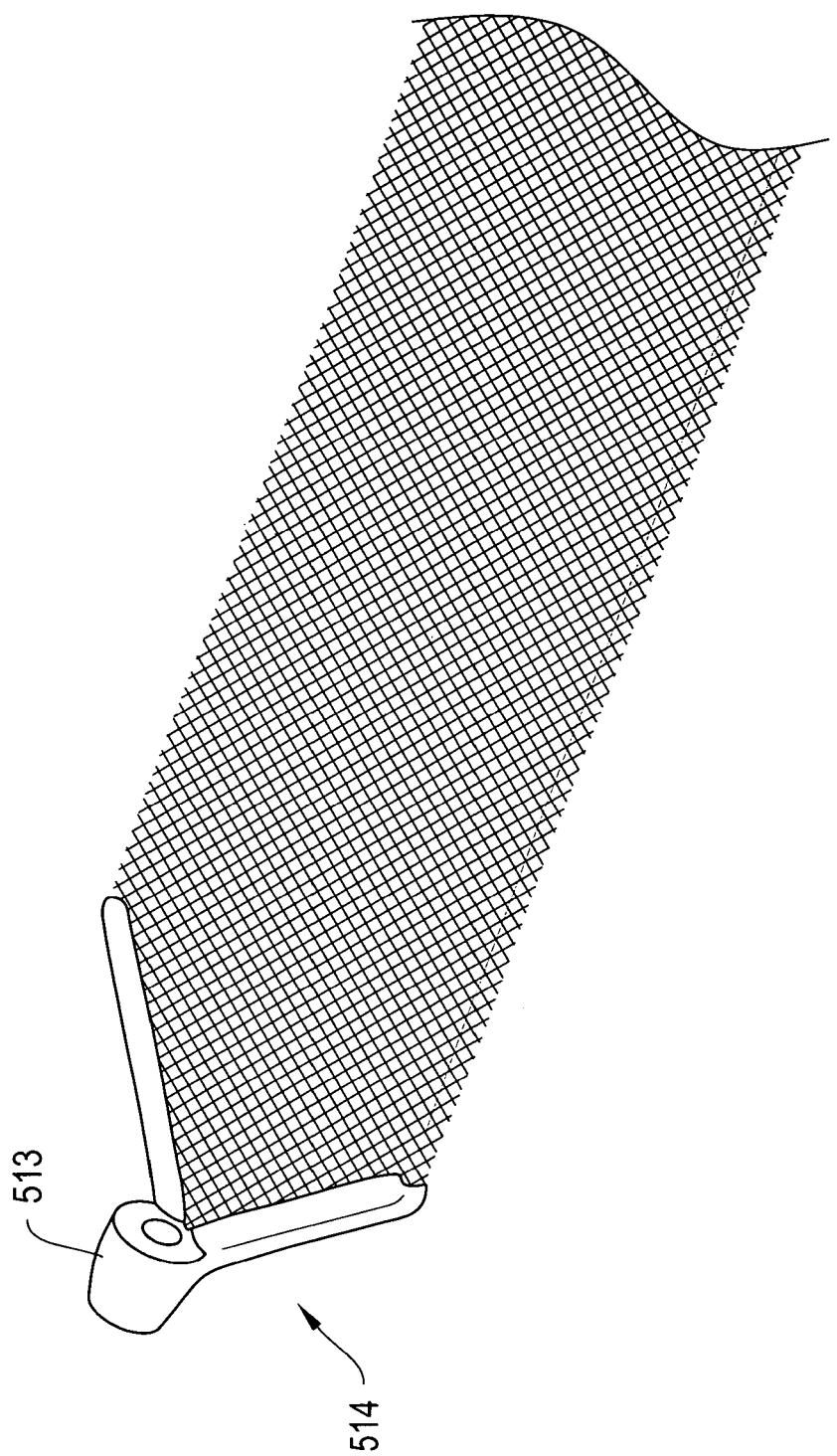
FIG. 7 shows the mesh strap of FIG. 5, with an alternative implant associator.

FIG. 7 shows the mesh strap 505 of FIGS. 5-6, with an alternative implant associator 514. The implant associator 514 includes a ring 513 that has circular cross-sections lying in a plane that is perpendicular to a plane of the mesh strap. The implant associator 514 is, in certain embodiments, used in operative combination with the delivery devices described herein. The alternative orientation of the ring 513 with respect to implant associator 514 in comparison to the ring 509 with respect to implant associator 510 results in a different orientation of the mesh strap 505 with respect to the delivery device 100 when the mesh strap 505 and the device 100 are coupled. This alternative orientation results in the strap 505 aligning with the end-region 120c of the head 120, as opposed to extending from the end-region 120c of the head 120 at about a 90 degree angle as illustrated in FIG. 6. The alternative orientation using implant associator 514 may be preferred by a medical operator when the operator is delivering the mesh strap 505 through a narrow anatomical incision and/or a narrow pathway through a patient's anatomy.

Other exemplary alternatives to implant associators 510 and 514 as well as alternate configurations for the tip 130 and/or end region 120c of the device 100 are disclosed in U.S. patent application Ser. No. 10/542,365 and U.S. patent application Ser. No. 11/152,898, the contents of which are incorporated by reference herein in their entirety.

Figure 8:
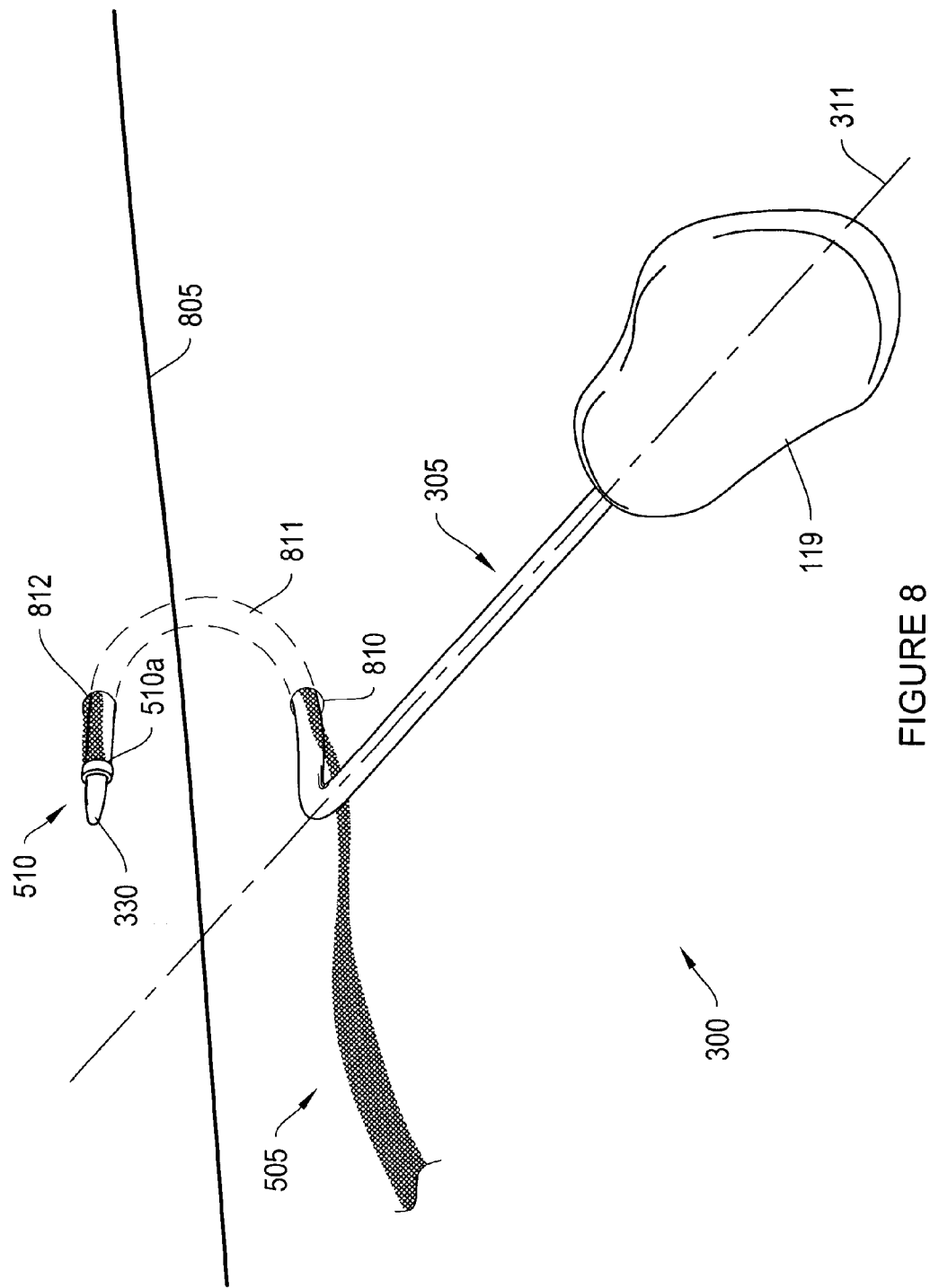
FIG. 8 illustrates the use of an exemplary pelvic floor device in implanting a mesh strap into tissue.

As noted above, the devices can be used to deliver implants to patient tissue. FIG. 8 more particularly depicts the use of device 300 of FIG. 3 to implant a mesh strap 505 through a region 810 of the levator ani muscle 810, more particularly, about the tendinous arch of the levator ani muscle or "white line" 805.

In operation, the operator associates the mesh strap 505 with the delivery device 300 using implant associator 510. The operator then places the tip 330 of the delivery device 300 proximal to a target tissue region 810. The operator rotates the device 300 counter clockwise along a longitudinal axis 311 of the shaft 305 of the device 300, applying sufficient force to the shaft 305 to cause the tip 300 to dissect tissue and trace a path 811 below and around the tendinous arch 805 of the levator ani muscle. The tip 330 exits the tissue near a tissue region 812, while the mesh strap 505 remains associated with the device 300 via implant associator 510. The user then retracts the device 300, leaving mesh strap 505 implanted in the levator ani muscle, by rotating the device 300 in a clockwise direction about the longitudinal axis 311. Upon retraction, the implant associator 510 dissassociates from the delivery device 300 when the back side 510a of the implant associator 510 abuts against the tissue surface near tissue region 812, thereby preventing the implant associator 510 from continuing in a retrograde direction along path 811. In certain embodiments, the mesh strap 505 includes tanged edges or barbs to help anchor the strap in surrounding tissue proximal to the path 811.

To assist in the retraction, the operator may use a tonged forceps instrument or other tong-like or tweezer-like instrument (not shown) to grasp and hold in place the implant associator 510 as the device 300 is retracted. In certain embodiments, the operator grasps the implant associator 510 with the forceps and pulls the implant associator 510 away from the tip 330, thereby dissassociating the mesh strap 505 from the delivery device 300, before retracting the delivery device 300. Optionally, after the delivery device 300 is retracted, the operator uses the forceps instrument to grasp the implant associator 510 and pull the implant associator 510 generally away from the tissue region 812. This allows the operator to tension an implant, as discussed further below.

Alternately, the operator can use the device 400 of FIG. 4 to carry out the above procedure. In such an implementation, the operator inserts the device 400 above the white line 805 using a clockwise rotation for insertion and a counterclockwise rotation for retraction. In that case, the insertion will be near tissue region 812, and the tip 430 will exit the tissue near region 810.

Figure 9:
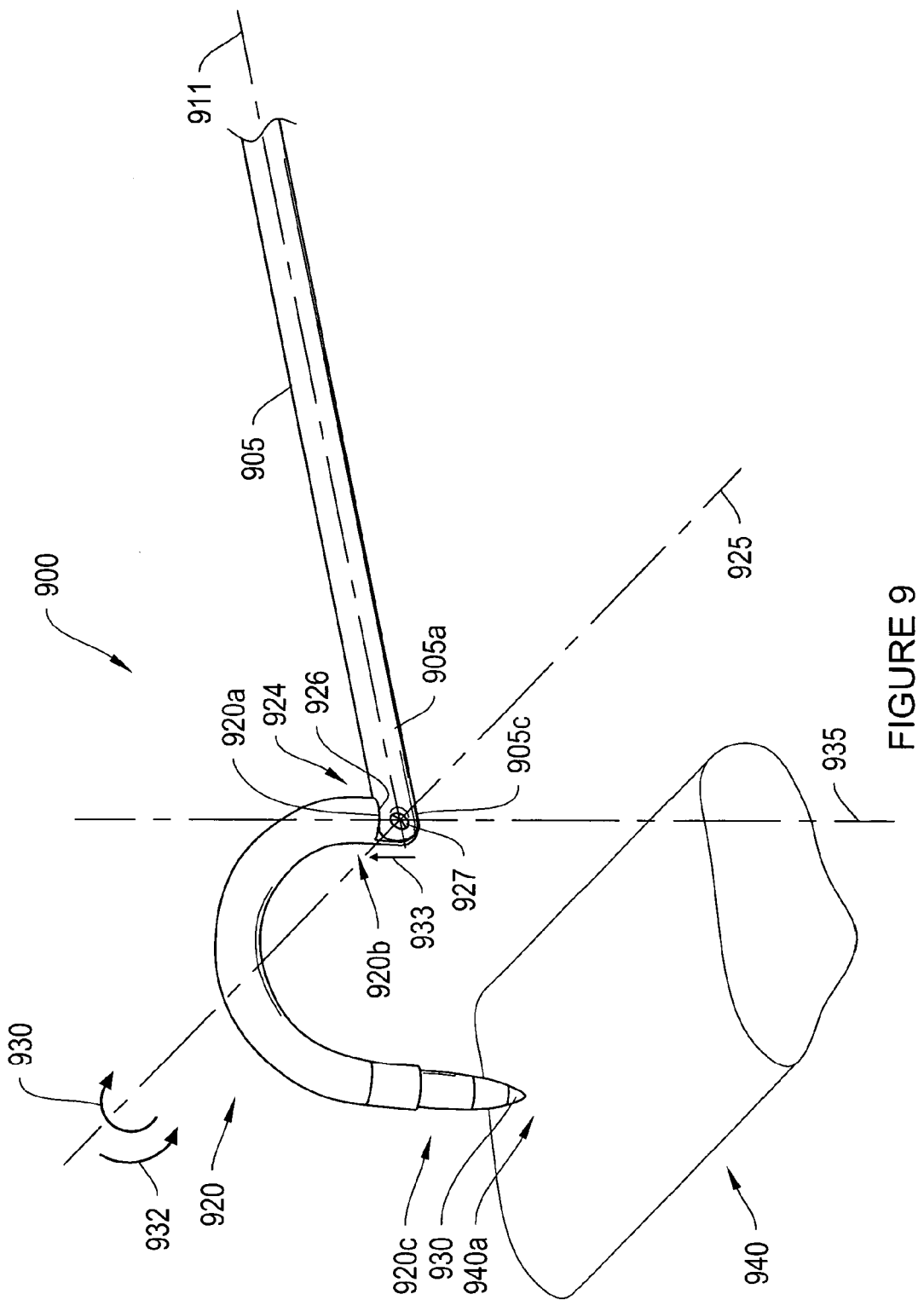
FIG. 9 shows an alternative embodiment of a pelvic floor delivery device having a rotatable head.

As shown, the devices described above include a head that is fixed to a shaft. In certain alternative embodiments, the head and shaft are configured to rotate with respect to each other, thereby allowing the operator to adjust the placement of the head without moving the shaft. FIG. 9 shows such an exemplary alternative delivery device 900 including a shaft 905 with a distal end 905a and a proximal end (not shown) opposite the distal end 905a, and a head 920, connected to the shaft 905 by pivotable junction 924.

The pivotable junction 924 allows the head 920 to rotate about the distal end 905a of the shaft 905, and in particular about an axis 925 in directions 930 and 932 without moving the shaft 905. As shown, the axis 925 is perpendicular to the longitudinal axis 911 of the shaft 905 and normal to the plane of the rotatable head 920.

In certain embodiments, the pivotable junction 924 is adjustable to fix the position of the head 920 with respect to the shaft 905 at a desired position. In particular, the depicted junction 924 may include a hinge and pin assembly for fitting into a slot 927 about which the head 920 rotates. The hinge 924 and pin assembly can be configured to provide sufficient tightness such that the rotatable head 920 can be manually rotated to a desired position upon application of appropriate mechanical force to the head 920, and then remain substantially fixed in that position upon insertion of the pin into the slot 927. The pin can be released from the slot 927 to allow the head 920 to freely rotate about the shaft 905, and then pushed fully into its slot 927 to fix the head 920 at a preferred orientation.

Also shown, the device 900 has a stop surface 926 that restricts the range of motion of the rotatable head 920. Operatively, a surface 920a of rotatable head 920 aligns with the stop surface 926, thereby preventing further rotation of the rotatable head 920 in the direction 930. The stop surface 926 can be oriented at varying angles with respect to the longitudinal axis 911 in order to alter the angle beyond which rotation is prevented. As described below, the rotatable head feature allows an operator to adapt the configuration of the head 920 to facilitate insertion into various anatomical locations of a patient.

In an alternative embodiment, the device 900 is configured to rotate about an axis 935, which is tangential to the rotatable head 920 at region 920b, where the head 920 meets the shaft 905. This embodiment enables an operator to modify the orientation of the head 920 to be similar to the 90 degree angled configurations of the heads 320 and 420 in FIGS. 3-4, or to be oriented with other preferred angles. In one exemplary embodiment, rotation about the axis 935 is accomplished by inserting a pin in the shaft 911, the pin's longitudinal axis being aligned with axis 935, at location 905c with a point of the needle extending in direction 933.

In still another embodiment, the junction 924 allows the device to rotate about any of axes 925, 935, and 911 independently or in combination. By way of example, the hinge may include a ball-and-socket joint. Any of the devices described herein may be configured with a pivotable junction 924. As shown, the shaft 905 and the head 920 of device 900 are substantially similar to the shaft 105 and the head 120 of the device 100 of FIG. 1, and the various alternative embodiments and features of other delivery devices described herein may apply to device 900.

Figure 10:
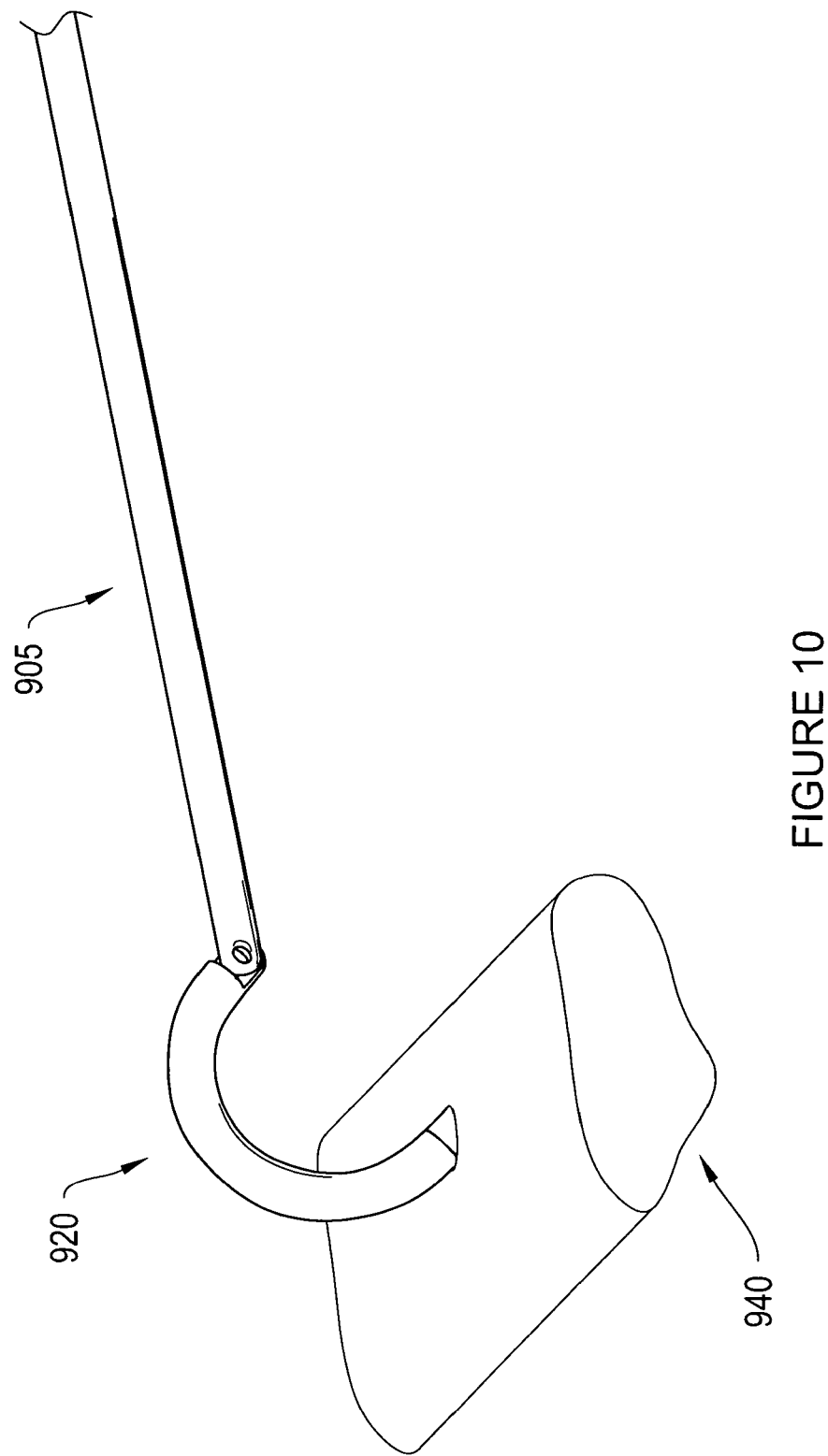
FIG. 10 illustrates the use of the device of FIG. 9 in penetrating tissue.

In operation, the device 900 can be used to secure one or more mesh straps of a surgical implant to a target tissue, for example the sacrospinous ligament or coccygeus muscle. In an exemplary method, an operator first couples a mesh strap 505 (not shown in FIG. 9) to the device 900 using an implant associator 510 (not shown in FIG. 9) as described above. The operator then positions the device 900 so that its tip 930 overlies a target region 940a of the tissue 940. Next, the operator applies appropriate torque to the device 900 from its handle (not shown) and thereby drives the tip through the tissue 940, as shown in FIG. 10 which depicts the head 920 partially disposed within the target tissue 940. The operator may position a forefinger on the head 920 for leverage, thereby rotating the head 920 about the pivotable junction 924 and driving the head 920 into the tissue 940 without moving the shaft 905.

Figure 11:
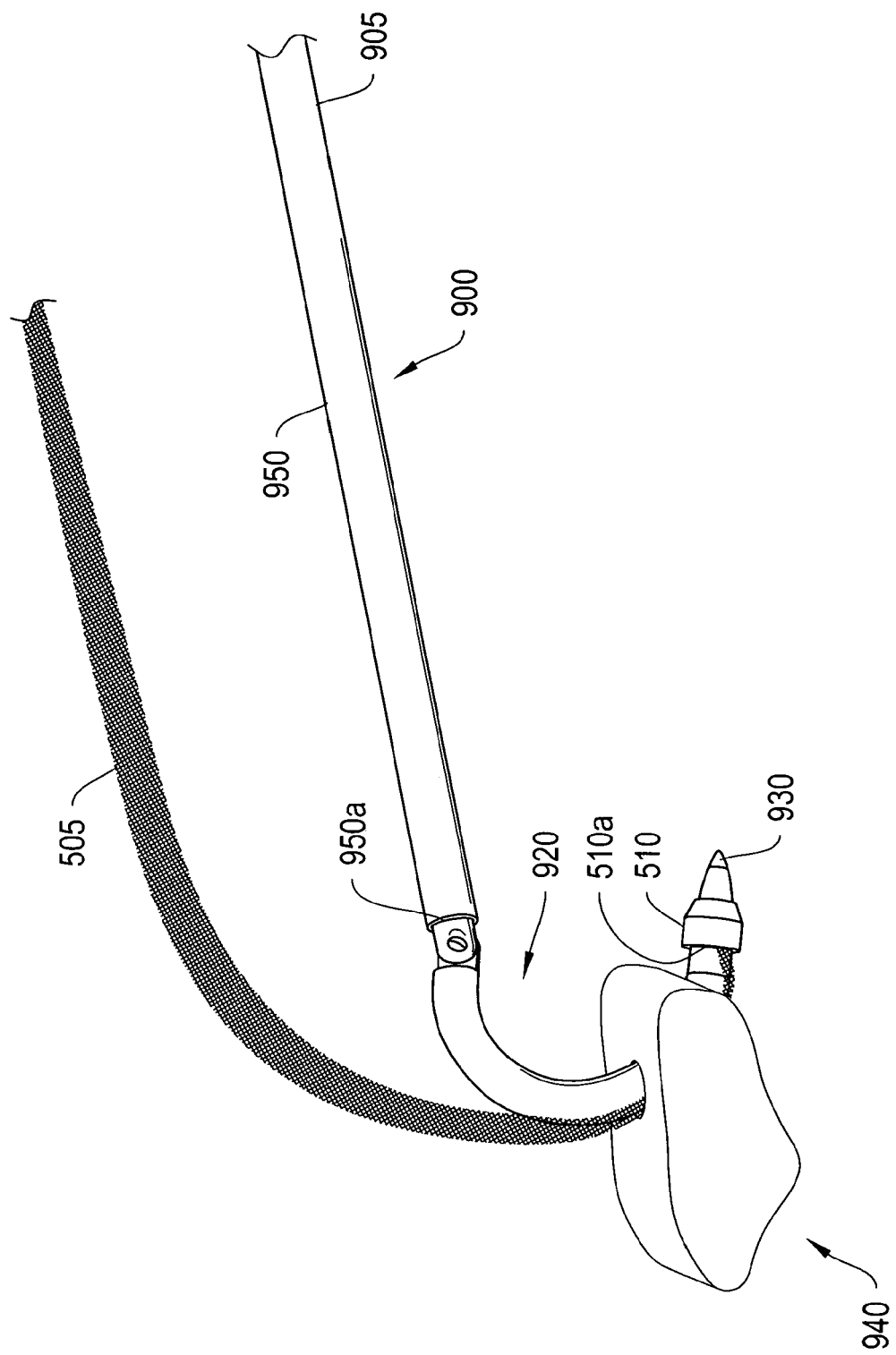
FIG. 11 shows the device of FIG. 9 in association with a mesh strap implant associator and penetrating through a target ligament.

FIG. 11 shows the device 900 with its tip 930 associated with mesh strap 505 through implant associator 510 after having penetrated through the target tissue 940. The operator drives the head 920 through the tissue 940, such that the tip 930, coupled with implant associator 510, emerges through the tissue 940. The operator then retracts the rotatable head 920, leaving the mesh implanted through the tissue 940 and anchored by the implant associator 510. Alternatively, an operator uses a forceps or other tong-like instrument to prevent the connector from retracting through the tissue 940 as discussed above. Also as discussed above, the mesh strap 505 may have tanged edges that help to anchor the strap in the ligament 940.

The delivery device 900 may, in one optional aspect, include a cannula 950 disposed about the shaft 905. The cannula 950 is operably coupled to the rotatable pivot head 920 and is configured to control rotation of the head 920. In particular, the cannula 950 includes a distal end 950a that rotates the end of the pivot head 920 near or in contact with the junction 924 as desired by an operator. The operator may use external control mechanisms, such as knobs and/or buttons located near the handle (not shown) to rotate the head 920.

Figure 12:
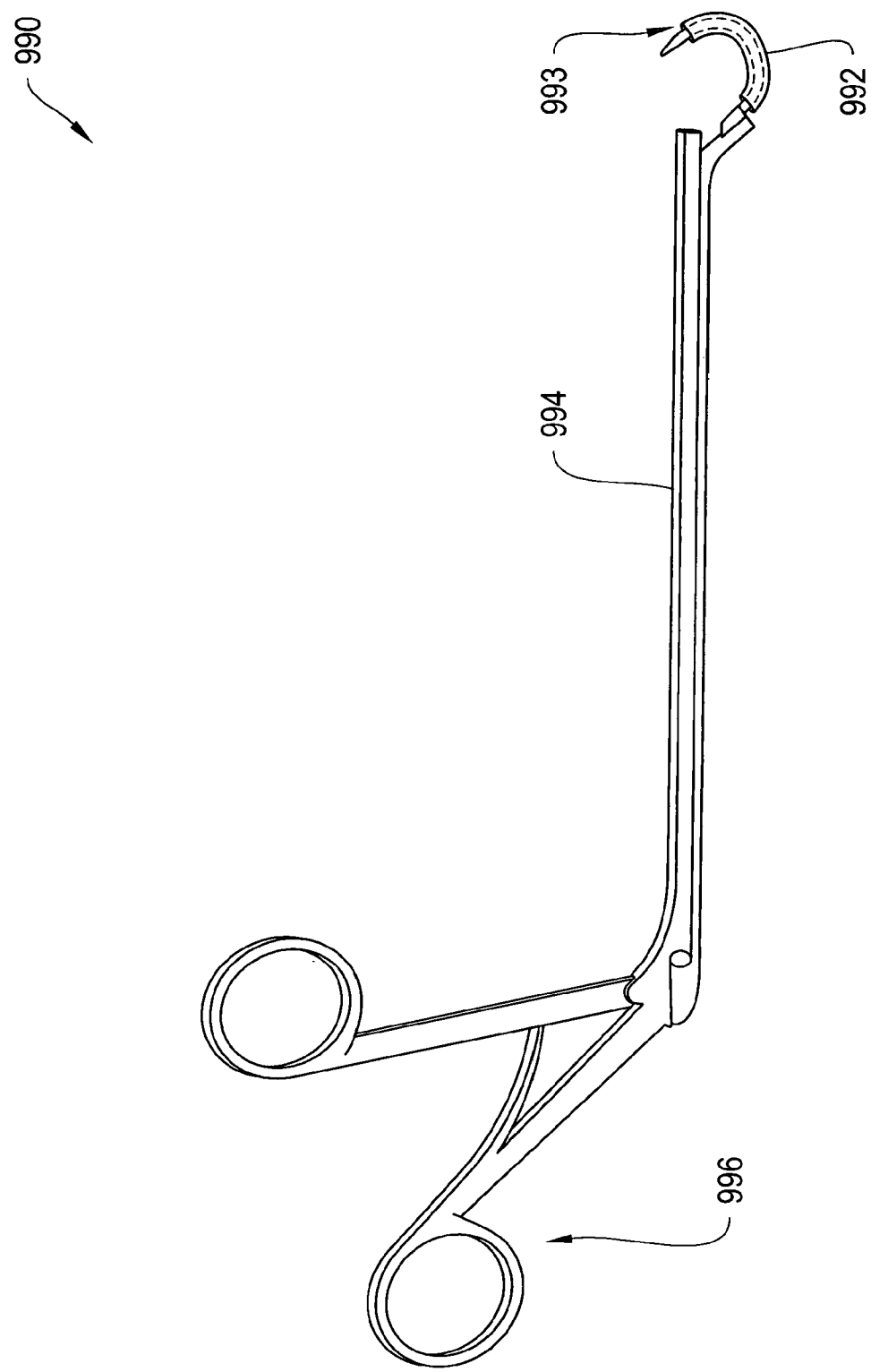
FIG. 12 shows a Miya device which may be used to place one or more mesh straps of an implant.

An another embodiment, a Miya hook 990, as shown in FIG. 12, may be modified and used to place one or more mesh straps of an implant. The Miya hook 990 includes a rounded head portion 992, a shaft 994, and scissor-like handles 996. The rounded head portion 992 and the shaft 994 are configured to rotate with respect to each other, thereby allowing the operator to adjust the placement of the head portion 992 without moving the shaft. The head portion 992 includes a shoulder 993, such that the tip of the head portion 992 may associate with an associator, such as implant associator 510 of FIG. 5.

Figure 13A:
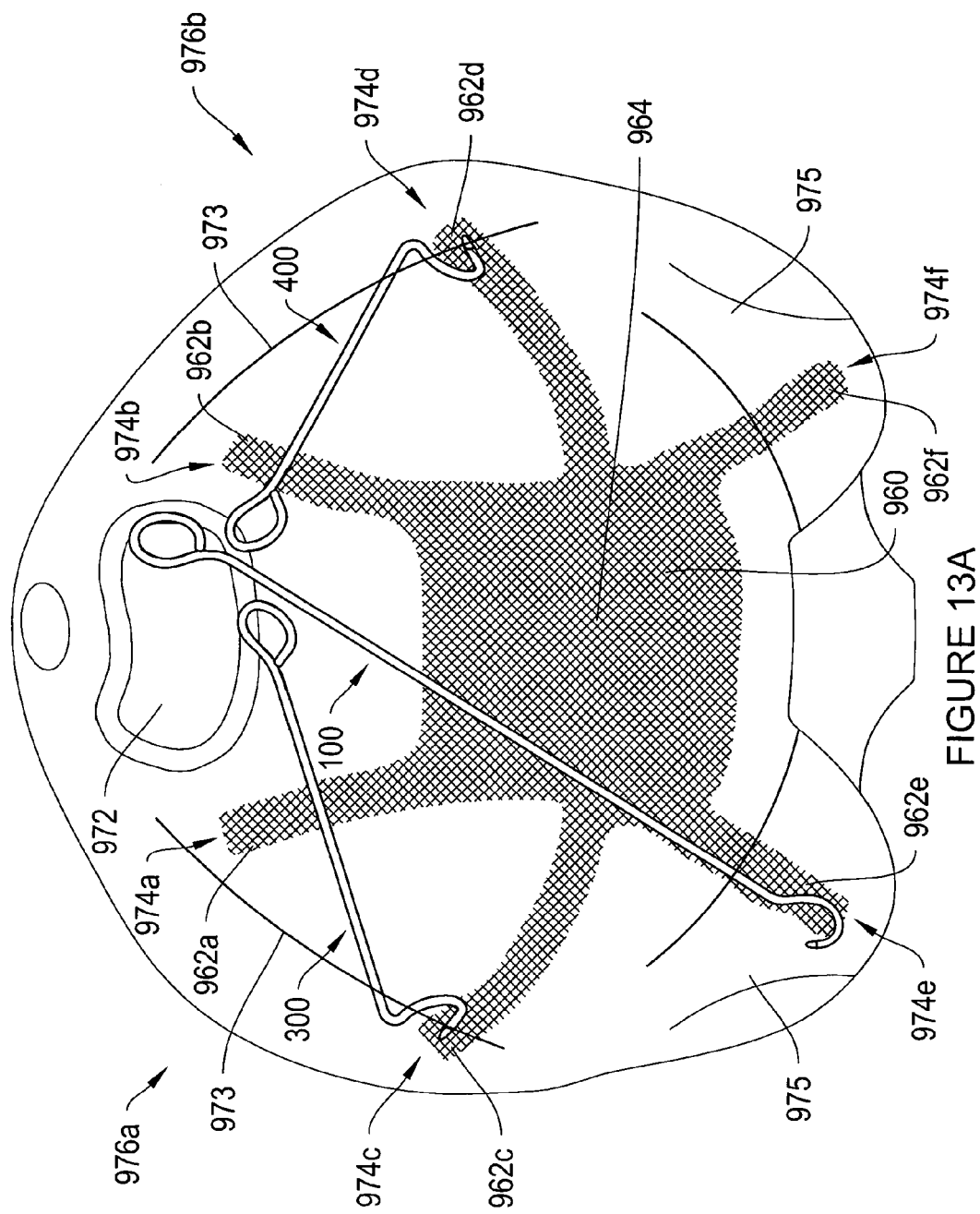
FIG. 13A illustrates an inferior view of a sling implanted within a patient using a device according to the invention.

The illustrative embodiments discussed above illustrate devices and methods for securing a mesh strap 505 to a target tissue, such as a muscle or a ligament. As mentioned above, the mesh strap 505 can be a portion of a larger surgical implant which can be used for pelvic floor support and/or repair. FIG. 13A depicts an inferior view of a pelvic floor implant 960 positioned within a patient by the use of one or more of the devices described herein. As shown, the implant 960 includes a central region 964 and a plurality of straps 962a-962f similar to mesh strap 505. The straps 962a-962f include two anterior straps 962a and 962b, and four posterior straps, 962c and 962e on one side, and 962d and 962f on the contra-lateral side.

While the depicted implant 960 includes 6 straps, more or fewer straps may be used depending on the nature of the condition being treated, and exemplary embodiments include 2, 3, 4, or 5 straps. For example, if a medical operator determines that a patient requires posterior support but not anterior support, an implant may consist of four straps 962c-962f, but not straps 962a-962b.

The mesh implant 960 is sized and shaped to fit on or near the pelvic floor and support the bladder, the vagina, and/or the rectum. The straps 962a-962f are spaced apart so as to align with particular anatomical locations within the pelvic region for securing the implant 960 thereto. As shown in the depicted example, the anterior straps 962a and 962b are positioned to align with the patient's obturator foramen (not shown, but generally located at regions 976a and 976b) and optionally can ultimately be pushed through the patient's obturator membranes. Posterior straps 962c and 962d are positioned to align with the tendinous arch of the levator ani muscle 973, only a portion of which is depicted in FIG. 13A, and posterior straps 962e and 962f are positioned to align with the sacrospinous ligament 975, only a portion of which is depicted in FIG. 12. In an alternative embodiment, the posterior straps 962c and 962d are placed in the iliococcygeus muscle. The posterior straps 962e and 962f may be positioned in the sacrospinous ligament and the coccygeus muscle, or alternatively, only in the coccygeus muscle. The mesh straps 962a-962f may include respective implant associators (not shown), similar to implant associator 510.

In one aspect, the devices and systems described herein may be used in surgical procedures to treat a patient suffering from pelvic floor disorders or urinary incontinence. An exemplary technique for implanting and securing the surgical mesh 960 in an anatomy of a patient is now described.

The exemplary technique consists of three phases. In a first phase, the operator inserts and secures the posterior straps 960e and 960f into the sacrospinous ligament, the coccygeus muscle, or both the sacrospinous ligament and coccygeus muscle. In a second phase, the operator inserts and secures the posterior straps 962c and 962d into the levator ani muscle, for example, the tendinous arch of the levator ani muscle or the iliococcygeus muscle. In a third phase, the operator inserts the anterior straps 962a and 962b through the obturator foramen and secures the straps in either obturator membranes or in the patient's tissues proximal to the obturator canals.

More particularly, in the first phase, to insert the strap 962e a medical operator creates an incision in a patient's anterior vaginal wall (not shown). The incision can be dissected or extended as required to facilitate access of delivery device 100 to target region 974e. Next, the operator couples, preferably external to the body, mesh strap 962e with delivery device 100 via an implant associator (not shown) similar to implant associator 510. The operator then inserts the device 100 and coupled mesh strap 962e through the vaginal opening 972, into the vaginal canal, and through the vaginal incision. The operator pierces and drives the mesh strap 962e through the target region 974e of the sacrospinous ligament, and then retracts the device, using methods similar to those described above. As mentioned above, the operator may use forceps to facilitate the disassociation of the delivery device 100 from the mesh strap 962e.

The operator then delivers the mesh strap 962f through the vaginal opening 972 and through the vaginal incision in a similar manner as 962e. The vaginal incision may be dissected or extended as necessary to facilitate access of delivery device 100 to target region 974f. The operator may use the same delivery device 100 for delivery of strap 962f, or alternatively may use a second delivery device 100.

The first phase can also be carried out using delivery device 900 of FIG. 9 or delivery device 101 of FIG. 1B instead of delivery device 100. The use of delivery device 900 is beneficial in part because the operator can adjust the rotation of the rotatable head 920 to suit the operator's preference and/or the particular anatomy of the patient. The use of delivery device 101 is beneficial in part because its curved shaft 103 may facilitate passage of the device through the vaginal canal in order to access the target regions 974e and 974f of the sacrospinous ligament.

In the second phase, the operator inserts the straps 962c and 962d into target regions 974c and 974d of the levator ani muscle. To insert strap 962c, the operator first couples delivery device 300 to the mesh strap 962c using an implant associator (not shown), then inserts the device 300 into the vaginal canal, and through the vaginal incision. The vaginal incision provides access to the target region 974c in part because the head 320 of the device 300 is rotated so its tip 330 aligns with the target region 974c. However, if the rotated head 320 does not align with target region 974c using the vaginal incision in a particular patient's anatomy, the operator can choose a device 900 and adjust the rotation of rotatable head 920 to align the tip 930 with target region 974c.

With the device 300 appropriately placed proximal to the target tissue region 974c, the operator then pierces and drives the mesh strap 962c through the target region 974c of the levator ani muscle, and retracts the delivery device 300 using the method discussed with respect to FIG. 8.

The operator similarly delivers mesh strap 962d to target region 974d of the tendinous arch of the levator ani muscle contra-lateral to target region 974c using delivery device 400. Similar to delivery device 300 accessing target region 974c, device 400 accesses target region 974d through the vaginal incision used to deliver strap 962f. Alternatively, the operator can choose a device 900 and adjust the rotation of rotatable head 920 to align the tip 930 with target region 974d.

In a third phase, the operator inserts the anterior straps 962a and 962b through the obturator foramen and secures the straps either to respective obturator membranes or to the patient's tissues proximal the obturator canals as discussed in, for example, U.S. patent application Ser. No. 10/957,926, the entire contents of which are incorporated by reference herein in their entirety.

More particularly, according to one method of use, an operator implants the anterior strips 962a and 962b using delivery devices that create passages through body tissue from an inferior pubic ramus through an obturator foramen to a location proximal the vaginal opening 972. The operator creates such a passage on each side of the patient. In order to create the passages, the delivery devices may include needles and/or dilators having curved portions that can trace paths through an obturator foramen located generally at 976a or 976b, through the vaginal incision in the anterior vaginal wall, and ultimately to a region externally accessible via vaginal opening 972. By way of example, FIG. 15A shows a delivery device 983 that can deliver anterior strap 962a, and FIG. 15B shows a delivery device 984 that can deliver anterior strap 962b. Alternatively, device 985, depicted in various perspectives in FIGS. 16A, 16B, and 16C, can deliver anterior strap 962b, while a symmetric device can deliver anterior strap 962a.

In one implementation of the anterior straps, two incisions are made on the body of the patient. A first incision is made just to the side of the edge of the ishiopubic ramus in the region of the urethral meatus. A second incision, corresponding to the first incision, is made on the contra-lateral side. In an inside-out approach, the strap 962a is associated with the delivery device 983 of FIG. 15A, which is inserted through the vaginal incision toward the obturator foramen. The delivery device 983 pierces the obturator membrane, and the tip of the delivery device 983 along with the end of the strap 962a exits the patient tissue through the first incision. The operator delivers and secures strap 962b by repeating this process symmetrically with delivery device 984 on the contra-lateral side of the body.

In an alternative approach, the operator extends the delivery device 983 to an anatomical position in front of the obturator membrane without piercing the membrane. In this approach, the strap 962a is configured with soft tissue anchor end portions for anchoring into the soft tissue in front of the membrane. Sling assemblies with soft tissue anchors and devices and methods for applying slings with soft tissue anchors are disclosed, for example, in commonly assigned U.S. patent application Ser. No. 11/400,111, filed Apr. 6, 2006 and entitled "Systems, Devices and Methods for Treating Pelvic Floor Disorders," U.S. patent application Ser. No. 11/399,913, filed Apr. 6, 2006 and entitled "Systems, Devices and Methods for Suburethral Support," and U.S. patent application Ser. No. 11/152,898, filed Jun. 14, 2005 and entitled "Systems, Methods and Devices Relating to Implantable Supportive Slings," the contents of each of which are incorporated by reference herein in their entirety.

In an outside-in approach, the delivery device 983 of FIG. 15A is inserted through one ishiopubic incision, piercing the obturator muscle and obturator membrane. A forefinger is placed in the vaginal incision and on the distal end of the delivery device. The forefinger is used to guide the distal end of delivery device 983 around the ishiopubic ramus through the vaginal incision.

Next, the operator associates strap 962a with the delivery device 983. The delivery device 983 and the mesh strap 962a can be associated with any of the implant associators discussed herein, or the implant association techniques discussed in U.S. patent application Ser. No. 10/542,365. For example, the delivery device 983 may include an L-slot near the distal tip, which may be used to associate the mesh strap 962a with the delivery device 983, such that the delivery device can pull the mesh strap 962a back out through the ischiopubic incision.

The delivery device 983 is then withdrawn from the ischiopubic incision, drawing the end of the mesh strap 962a through the passage created by the delivery device 983. Finally, the operator delivers and secures strap 962b by repeating this process symmetrically with delivery device 984 on the contra-lateral side of the body.

Figure 13B:
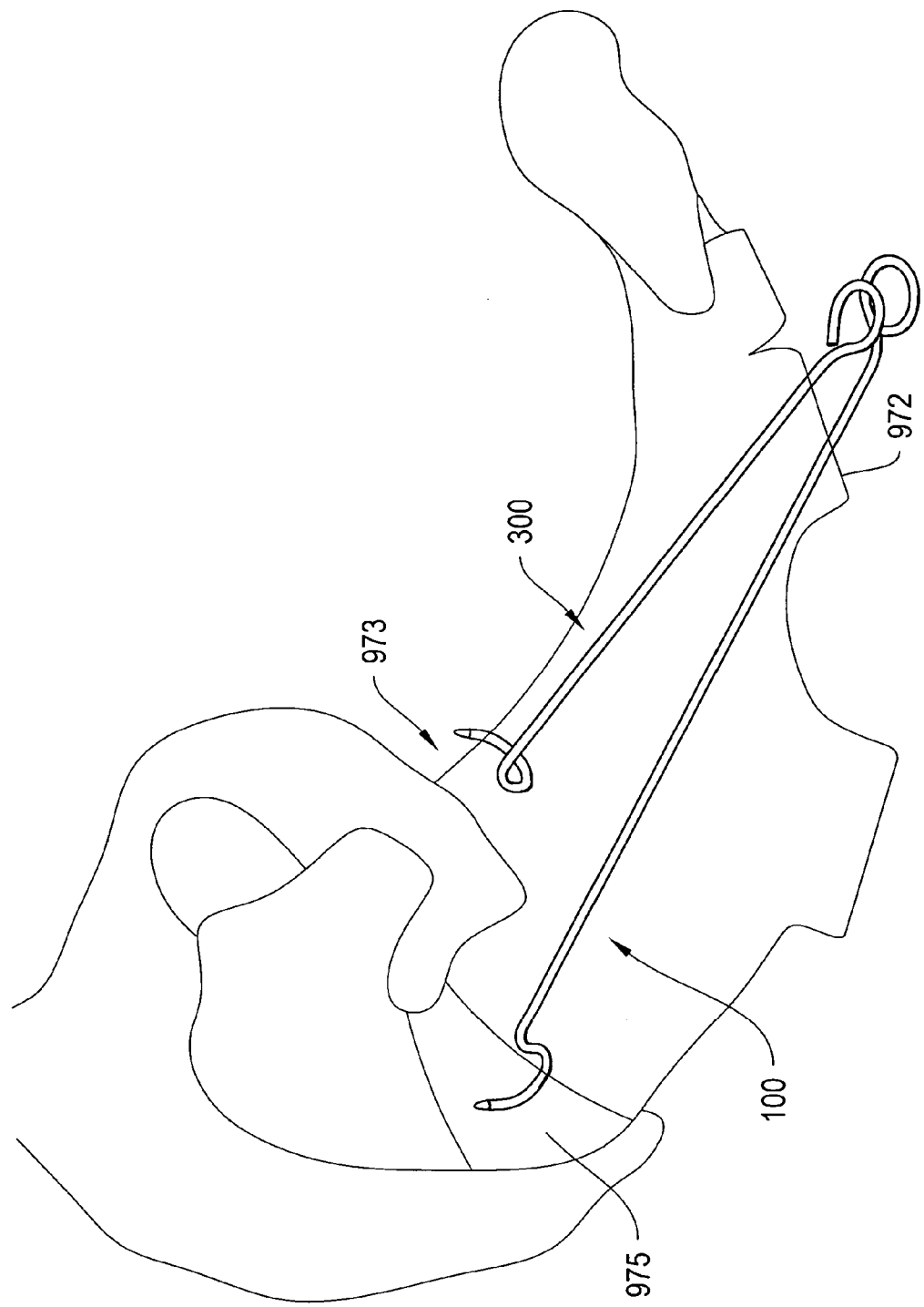
FIG. 13B illustrates a lateral view of the sling implant illustrated in FIG. 13A.

FIG. 13B shows a lateral view of the pelvic region of the patient, and more particularly shows the device 100 aligned with the sacrospinous ligament 975, and the device 300 aligned with the tendinous arch of the levator ani muscle 973, of which only a portion is shown. The implant 960 is not shown.

The straps and incisions need not be inserted or made, respectively, in the order described above. An operator can choose any suitable order for creating incisions and delivering straps 962a-962f. The operator, at his discretion, optionally performs one or more cystoscopies after inserting one or more of the mesh straps 962a-962f to check for damage to the bladder.

In one embodiment, for posterior pelvic floor support, the anterior straps 962a-962b may be cut off or otherwise removed from the implant 960. The anterior straps 962a-962b may be removed from the implant 960 before implantation. In this embodiment, the central region 964 of the implant 960 may be sutured or otherwise attached to the pubococcygeus muscle and/or the anterior portion of the tendinous arch of the levator ani muscle.

The exemplary three phase technique described above employed various ones of the delivery devices 100, 101, 300, 400, 983, 984, 985, and/or 900 to delivery various ones of the straps 962a-962f. Each of these devices can be provided with a handle 119 shown in FIG. 8 that is color-coded to match the color of the implant associator corresponding to the mesh strap 962a-962f that the device delivers. The operator can thereby visually identify which of the devices 100, 101, 300, 400, 983, 984, 985, and/or 900 will deliver which of the straps 962a-962f. Since certain devices, such as device 100, can be used to deliver multiple straps, the device 100 may include a handle 119 with multiple color codes. Other visual indications or markers may also be used.

Other delivery methods can be used for implant 960. For example, suprapubic, prepubic, and transvaginal approaches, disclosed in the patents and patent applications cited herein, can be used to delivery one or more of the straps 962a-962f. All operative combinations between the disclosed delivery devices and these alternative procedures are contemplated. Any of the delivery devices described above may be employed to create appropriate passageways to target regions in a patient's anatomy.

After the mesh straps 962a-962f are in place near their respective target regions 974a-f, the operator adjusts the tension of the implant 960 by pulling the mesh straps 962a-962f further through their respective target tissue regions. In certain implementations, an operator inserts a forceps through one of the vaginal incisions to one of the target regions 962a-962f. The operator may grasp and pull a respective implant associator (not shown) and thereby pull the respective mesh strap 962a-962f further through its tissue or ligament, as described above. This increases the tension of the implant. The operator may perform this process for one or more of the mesh straps until the desired tension is achieved.

Other methods of delivering and securing the mesh are envisioned. In some embodiments, the mesh straps, such as mesh straps 962a-962f, are not driven through muscle or ligament, but instead are anchored into general surrounding tissue by barbs or tangs on the edges and/or surfaces of the implant 960 and/or its straps 962a-962f. The straps 962a-962f can alternately be secured to soft tissue regions of the pelvic floor using soft tissue anchors as discussed in U.S. Provisional Application No. 60/715,362, the contents of which are incorporated herein by reference in their entirety. Alternatively, one or more of the straps 962a-962f may be secured to target tissue regions by suturing the straps. For example, straps 962c-f can be sutured to target tissue regions of the levator ani muscle and/or the sacrospinous ligament.

In another aspect, the invention includes a kit with devices for use in supporting or repairing pelvic floor problems. FIG. 14 illustrates an exemplary surgical kit 980 for use in surgery related to pelvic floor repair. The kit 980 includes these devices—device 100, device 300, and device 400. In certain embodiments, the shafts 305 and 405 are about equal in length and shaft 105 is between about 15% and 60% longer than shafts 305 and 405. In certain embodiments, shaft 105 is about 20% longer than shafts 305 and 405.

Optionally, the kit also includes one or more surgical implants, such as the implant 960. In this illustration, the straps 962a-962f are coupled with respective implant associators similar to implant associator 510, however in alternate embodiments the implant associators can be provided in the kit separate from the straps 962a-962f or may not be provided at all.

In another optional embodiment, the kit 980 includes one or more of the devices 983 and 984 of FIG. 15A and FIG. 15B. Additionally or alternatively, the kit 980 may include one or more of device 985 of FIGS. 16A-16C, as well as a symmetric device for use on a contra-lateral side of a patient. The kit 980 may additionally or alternatively include one or more of the delivery devices discussed in U.S. patent application Ser. No. 10/957,926 and/or device 101 of FIG. 1B. In alternative embodiments, device 900 is provided with (or without) one or more of the devices included in kit 980.

FIGS. 15A and 15B depict a pair of delivery devices 983 and 984, each having an angled handle, according to another illustrative embodiment of the invention. The devices 983 and 984 are substantially mirror images of each other for ease of use on either side of a patients body. Accordingly, for illustrative purposes, only FIG. 12A is discussed. The handle 987 of the delivery device 983 includes a first section 987a extending along a first longitudinal axis substantially in a first plane. A second section 987b of the handle 987 extends distally from, but at an angle to, the axis of the first section 987a. The first 987a and second 987b sections of the handle 987 are substantially coplanar in the first plane. A shaft 989 includes a curved section that extends from a mounting location at a distal end of the second handle section 987b. The curved section first extends out of the first plane of the first 987a and second 987b handle sections, then extends back toward the first plane. In some configurations, the distal tip 989a (conically shaped in the illustrative embodiment) of the delivery device 983 extends back through the first plane. In other configurations, the distal tip 989a extends up to or short of the first plane. According to one feature, the shaft 989 rotates about an axis that is substantially orthogonal to the first plane. However, according to other illustrative embodiments, the axis need not be substantially orthogonal to the first plane. According to alternative illustrative embodiment, at least one of the first 987a and second 987b sections of the handle 987 tapers to have a narrower width as the handle 987 extends distally toward the shaft.

FIGS. 16A-16C depict various views of a delivery device 985 having a handle 991 with first 991a and second 991c substantially straight sections located substantially in a first plane and angled relative to each other at 991b, a transitional portion 993 extending out of a distal end of the handle 991, and a shaft 995 extending from a distal end of the transitional portion 993. The shaft includes curved section 995a, a straight section 995b, and terminates in a conical tip 995c.

The transitional portion 993 interfits and extends axially out of the distal end of the second handle section 991c to affix the shaft 995 to the handle 991. As a result, the transitional portion 993 is substantially co-planar with the handle 991 in the first plane. The curved section 995a of the shaft 995 extends from a distal end of the transitional portion 993. The straight section 995b of the shaft 995 extends from a distal end of the curved section 995a. The curved section 995a and the straight section 995b are substantially coplanar in a second plane. According to the illustrative embodiment of FIGS. 16A-16C, the first and second planes are substantially orthogonal to each other. However, the first and second planes may be at any suitable angle (e.g., about 10, 20, 30, 45, 60, 70 or 80 degrees) to each other. In another illustrative embodiment of FIGS. 16A-16C, the first and second sections 991a and 991c of the handle 991 are at an angle of about 150 degrees to each other. However, first and second sections 991a and 991c of the handle 991 may be at any suitable angle (e.g., about 80, 90, 100, 110, 120, 130, 140, 160, 170 or 180 degrees) to each other.

To provide structural reinforcement, sections 991b and 991c have a cross sectional diameter that tapers to be smaller at the distal end 143 of the handle 991. Additionally, rather than having the tapered section of the transitional portion being formed as part of the shaft, the tapered portions 991a, 991b, and 991c of the embodiment of FIG. 16 are formed as part of the handle 991. According to one feature, this configuration reduces the length of the transitional portion 993 and thus, provides improved structural support for the curved section 995a. Preferably, in operation, neither the handle 991 nor the transitional portion 993 extends into the body of the patient, and the angle at transitional portion 993 provides a positive stop against this occurring.

As mentioned above, the surgical implants of this invention, such as implant 960 of FIG. 14, are typically a mesh material. There are many possible mesh materials, and the sling may, in the alternative or in combination, be made of other types of materials. Exemplary mesh materials include, for example, synthetic materials, natural materials (e.g., biological) or a combination thereof. The mesh may be fabricated from any of a number of biocompatible materials, such as nylon, silicone, polyethylene, polyester, polyethylene, polyimide, polyurethane, polypropylene, fluoropolymers, copolymers thereof, combinations thereof, or other suitable synthetic material(s). The material may be, for example, a biodegradable synthetic material. The term "biodegradable," as used herein, refers to the property of a material that dissolves in the body. Such materials may also be absorbed into the body, i.e., bioabsorbable.

Suitable bioabsorbable synthetic materials include, without limitation, polylactic acid (PLA), polyglycolic acid (PGA), poly-L-lactic acid (PLLA), poly(amino acids), polypeptides, human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, a material that has a single direction where the tensile strength of the material is the highest. Oriented materials may include rectus fascia and/or facia lata, as well as oriented synthetic materials.

Exemplary biodegradable polymers, which may be used to form the tubular mesh 100, in addition to those listed above, include, without limitation, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(tert-butyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, poly(phosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan, alginates and regenerate cellulose; poly(amino acid) and proteins, such as poly(lysine), Poly (glutamic acid), gelatin and collagen; and mixtures and copolymers thereof.

The implant 960, either as a whole or on a fiber by fiber basis, may include an agent for release into the patient's tissues. One illustrative agent is a tissue growth factor that promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the biodegradable materials. This may be controlled by selecting differing methods for loading the agent onto the sling. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues. Besides applying active pharmaceutical agents, passive agents may be applied to promote tissue ingrowth. For example, titanium sputtering or chrome sputtering can be used.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, predival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacin, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as ϵ-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papavereturn, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the slings of the invention include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetyl salicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenyl-propylamine, tropenzile, trospium chloride, xenytropium bromide, and pharmaceutically acceptable salts thereof.

According to another feature, the implants, such as implant 800, of the invention may include any suitable end portions, such as tissue dilators, anchors, and association mechanisms for associating the sling with the delivery devices of the invention. They may also include other slings, sling assemblies, sling delivery approaches, sling assembly-to-delivery device association mechanisms, and sling anchoring mechanisms. These and other features with which the delivery devices, implants, methods, and kits of the invention may be employed are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," U.S. Pat. No. 6,197,036, entitled "Pelvic Floor Reconstruction," U.S. Pat. No. 6,691,711, entitled "Method of Correction of Urinary and Gynecological Pathologies Including Treatment of Incontinence," U.S. Pat. No. 6,884,212, entitled "Implantable Article and Method," U.S. Pat. No. 6,911,003, entitled "Transobturator Surgical Articles and Methods," U.S. patent application Ser. No. 10/840,646, entitled "Method and Apparatus for Cystocele Repair," U.S. application Ser. No. 10/834,943, entitled "Method and Apparatus for Treating Pelvic Organ Prolapse," U.S. patent application Ser. No. 10/804,718, entitled "Prolapse Repair," and U.S. patent application Ser. No. 11/115,655, entitled "Surgical Implants and Related Methods," U.S. patent application Ser. No. 11/400,111, entitled "Systems, Devices, and Methods for Treating Pelvic Floor Disorders," and U.S. patent application Ser. No. 11/399,913, entitled "Systems, Devices, and Methods for Sub-Urethral Support". It is intended that the scope of the invention not be limited by this detailed description.

The present disclosure contemplates all combinations of features and elements disclosed herein. For example, various embodiments of delivery devices, transfer pins, implants, implant associators, and other features described herein are interchangeable with one another, unless explicitly stated otherwise. As such, combinations of these embodiments, if not explicitly disclosed, are contemplated and within the scope of the present disclosure.

The contents of all references, patents and published patent applications cited throughout this application, as well as their associated figures are hereby incorporated by reference in entirety.

The Figures and drawings referred to herein are not necessarily to scale; emphasis instead is generally placed upon illustrating the principles of the illustrated embodiments.

Variations, modifications, and other implementations of what is described herein will occur to those of ordinary skill without departing from the spirit and the scope of the present disclosure. Hence, many equivalents to the specific systems, methods, and other embodiments described herein exist and are considered to be within the scope of the present disclosure. For additional illustrative features that may be used with the present disclosure, including the embodiments described here, refer to the documents listed herein above and incorporated by reference in their entirety. All operative combinations between the above described illustrative embodiments and those features described in the documents incorporated by reference herein are considered to be potentially patentable embodiments of the claimed invention.

What is claimed is:

1. A method for delivering to a patient an implant with a central region and at least four extensions, comprising:
associating a first extension of the implant to a first delivery device, the first delivery device having a shaft with a curved distal portion, the shaft including a proximal end portion defining a handle, the handle including a curved shaft portion configured to be grasped by an operator of the first delivery device;
securing the first extension of the implant to at least one of a sacrospinous ligament and a levator ani muscle on a first side of a patient with the first delivery device;
securing a second extension of the implant to at least one of a sacrospinous ligament and a levator ani muscle on a contralateral side of the patient;
associating a third extension of the implant with a second delivery device, the second delivery device having a shaft with a curved distal portion, the curved distal portion of the shaft of the second delivery device being different than the curved distal portion of the shaft of the first delivery device, the shaft of the second delivery device being shorter than the shaft of the first delivery device;
delivering the third extension of the implant through an obturator foramen on the first side of the patient with the second delivery device; and
delivering a fourth extension of the implant through an obturator foramen on the contralateral side of the patient.

2. The method of claim 1, wherein the second extension of the implant is secured to at least one of the sacrospinous ligament and the levator ani muscle with a third delivery device, the third delivery device having a shaft with a curved distal portion, the curved distal portion of the shaft of the third delivery device being different from the curved distal portion of the shaft of the first delivery device and the curved distal portion of the shaft of the second delivery device.

3. The method of claim 2, further comprising securing a fifth extension to at least one of a sacrospinous ligament and a levator ani muscle on the first side of a patient, and securing a sixth extension to at least one of a sacrospinous ligament and a levator ani muscle on the contralateral side of the patient.

4. The method of claim 3, comprising securing the fifth extension with a delivery device different from the first delivery device, different from the second delivery device, and different from the third delivery device.

5. The method of claim 1, wherein the curved distal portion of the first delivery device includes a tip, and the securing the first extension of the implant to the sacrospinous ligament or the levator ani muscle includes rotating the shaft of the first delivery device such that tip is rotated through the sacrospinous ligament or the levator ani muscle.

6. The method of claim 1, wherein the first extension is coupled to an implant associator having a member that defines a through-hole, wherein the first extension is associated with the first delivery device by inserting a tip of the curved distal portion of the shaft of the first delivery device through the through-hole of the implant associator.

7. The method of claim 6, wherein the curved distal portion of the shaft of the first delivery device defines a shoulder proximate to the tip such that the tip is inserted through the through-hole until the shoulder engages with a portion of the implant associator defining the through-hole.

8. The method of claim 1, wherein the curved distal portion of the shaft of the first delivery device includes a tip having a reduced diameter section, the tip intersecting with a longitudinal axis of the shaft of the first delivery device.

9. A method for delivering an implant to a patient, the method comprising:
securing a first extension of the implant to a sacrospinous ligament on a first side of the patient with a first delivery device, the first delivery device having a shaft with a curved distal portion and a tip having a reduced diameter section, the tip intersecting with a longitudinal axis of the shaft;
securing a second extension of the implant to a sacrospinous ligament on a second side of the patient with the first delivery device;
securing a third extension of the implant to a levator ani muscle on the first side of the patient with a second delivery device, the second delivery device having a shaft with a curved distal portion, the curved distal portion of the shaft of the second delivery device being different than the curved distal portion of the shaft of the first delivery device, the curved distal portion of the shaft of the second delivery device being disposed in a plane normal to a longitudinal axis of the shaft of the second delivery device, the shaft of the second delivery device being shorter than the shaft of the first delivery device; and
securing a fourth extension of the implant to a levator ani muscle on the second side of the patient with the second delivery device; and
securing a fifth extension of the implant to an obturator foramen with a third delivery device.

10. The method of claim 9, wherein the securing the first extension of the implant includes rotating the shaft of the first delivery device along the longitudinal axis of the shaft of the first delivery device such that the tip is rotated into the sacrospinous ligament.

11. The method of claim 9, wherein the shaft of the first delivery device defines a handle on a proximal end portion of the shaft of the first delivery device, the proximal end portion of the shaft defining a curved shaft portion configured to be grasped by an operator of the first delivery device.

12. The method of claim 9, wherein the third delivery device has a shaft with a curved distal portion, the curved distal portion of the shaft of the third delivery device being different from the curved distal portion of the shaft of the first delivery device and the curved distal portion of the shaft of the second delivery device.

13. The method of claim 9, wherein the first extension of the implant is coupled to a ring, and a tip of the curved distal portion of the shaft of the first delivery device is inserted into the ring.

14. The method of claim 9, wherein the securing the first extension includes positioning the first extension proximate to the sacrospinous ligament on the first side of the patient using the first delivery device and driving the tip of the shaft of the first delivery device into the sacrospinous ligament.

15. The method of claim 14, wherein driving the tip of the shaft of the first delivery device through the sacrospinous ligament includes placing the tip against the sacrospinous ligament, and applying pressure directly to the curved distal portion of the shaft of the first delivery device.

16. The method of claim 14, wherein driving the tip of the curved distal portion of the shaft of the first delivery device through the sacrospinous ligament includes placing the tip against the sacrospinous ligament, and twisting a handle of the first delivery device such that the tip is rotated into the sacrospinous ligament.

17. The method of claim 9, wherein the first extension is coupled to an implant associator having a member that defines a through-hole, wherein the first extension is associated with the first delivery device by inserting a tip of the curved distal portion of the shaft of the first delivery device through the through-hole of the implant associator.

18. The method of claim 17, wherein the curved distal portion of the shaft of the first delivery device defines a shoulder proximate to the tip such that the tip is inserted through the through-hole until the shoulder engages with a portion of the implant associator defining the through-hole.

19. The method of claim 9, wherein the first extension has a first color, and a handle of the first delivery device has the first color.

20. The method of claim 9, further comprising securing a sixth extension of the implant to an obturator foramen on the second side of the patient.

21. The method of claim 9, wherein the securing the first extension includes suturing the first extension to the sacrospinous ligament.

\* \* \* \* \*